(12) United States Patent
Sakai et al.

(10) Patent No.: US 8,911,908 B2
(45) Date of Patent: Dec. 16, 2014

(54) FUEL CELL AND ENZYME ELECTRODE

(75) Inventors: Hideki Sakai, Kanagawa (JP); Takaaki Nakagawa, Kanagawa (JP); Hideyuki Kumita, Kanagawa (JP); Hiroki Mita, Kanagawa (JP); Yasuhide Hosoda, Kanagawa (JP); Taiki Sugiyama, Kanagawa (JP); Ryuhei Matsumoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 729 days.

(21) Appl. No.: 13/121,985

(22) PCT Filed: Aug. 6, 2009

(86) PCT No.: PCT/JP2009/063936
§ 371 (c)(1),
(2), (4) Date: Mar. 31, 2011

(87) PCT Pub. No.: WO2010/041511
PCT Pub. Date: Apr. 15, 2010

(65) Prior Publication Data
US 2011/0236770 A1  Sep. 29, 2011

(30) Foreign Application Priority Data

Oct. 6, 2008 (JP) .............................. P2008-259963
Feb. 20, 2009 (JP) .............................. P2009-038676

(51) Int. Cl.
*H01M 8/16* (2006.01)
*H01M 4/90* (2006.01)
*C12Q 1/00* (2006.01)

(52) U.S. Cl.
CPC ................ *H01M 8/16* (2013.01); *Y02E 60/527* (2013.01); *H01M 4/9008* (2013.01); *C12Q 1/001* (2013.01)
USPC .......................................................... 429/401

(58) Field of Classification Search
USPC .......................................................... 429/401
See application file for complete search history.

(56) References Cited

U.S. PATENT DOCUMENTS

2005/0233189 A1* 10/2005 Shioya ............................ 429/19
2006/0210867 A1* 9/2006 Kenis et al. ................... 429/101

(Continued)

FOREIGN PATENT DOCUMENTS

JP  2006-058289  3/2006
JP  2006-093090  4/2006

(Continued)

OTHER PUBLICATIONS

International Search Report dated Oct. 30, 2009, for corresponding Patent Application No. PCT/JP2009/063936.

*Primary Examiner* — Muhammad Siddiquee
(74) *Attorney, Agent, or Firm* — Sony Corporation

(57) ABSTRACT

Provided is a fuel cell that is high in performance capabilities of initial power generation and in volume power density, and produces a stable power. Between fixing plates, first and second cell portions are provided. The first cell portion includes an anode, a cathode, and a proton conductor, and the second cell portion includes an anode, a cathode, and a proton conductor. To a space formed by gas-liquid separation and permeable films, cathode spacers, and an anode spacer, a fuel solution is filled. The gas-liquid separation and permeable films are disposed between the fixing plate and the cathode, and between the fixing plate and the cathode. The cathode spacers are provided around the cathodes, respectively, and the anode spacer is provided between the anodes.

16 Claims, 16 Drawing Sheets

(56) References Cited

U.S. PATENT DOCUMENTS

| | | | |
|---|---|---|---|
| 2007/0056852 A1 | 3/2007 | Kubo et al. | |
| 2007/0131546 A1 | 6/2007 | Nomoto et al. | |
| 2007/0184674 A1* | 8/2007 | Koch | 439/39 |
| 2007/0196722 A1* | 8/2007 | Tomita et al. | 429/43 |
| 2007/0218345 A1* | 9/2007 | Sakai et al. | 429/43 |
| 2007/0224466 A1* | 9/2007 | Nakagawa et al. | 429/13 |
| 2007/0235331 A1* | 10/2007 | Simpson et al. | 204/403.01 |
| 2008/0248354 A1 | 10/2008 | Kubo et al. | |
| 2008/0292912 A1* | 11/2008 | Logan et al. | 429/2 |
| 2009/0047567 A1 | 2/2009 | Sakai et al. | |
| 2009/0192297 A1* | 7/2009 | Yoshida et al. | 530/402 |

FOREIGN PATENT DOCUMENTS

| | | |
|---|---|---|
| JP | 2006-234788 | 9/2006 |
| JP | 2007-163185 | 6/2007 |
| JP | 2007-188810 | 7/2007 |
| JP | 2007-280944 | 10/2007 |
| JP | 2008-047461 | 2/2008 |
| JP | 2008-282586 | 11/2008 |
| JP | 2009-049012 | 3/2009 |
| JP | 2009-117088 | 5/2009 |
| JP | 2009-158466 | 7/2009 |
| WO | 2006/057387 | 6/2006 |
| WO | 2007/088975 | 8/2007 |
| WO | 2008/058165 | 5/2008 |

* cited by examiner

FUEL CELL AND ENZYME ELECTRODE

CROSS REFERENCE TO RELATED APPLICATIONS

The present application is a National Stage of International Application No. PCT/JP2009/063936 filed on Aug. 6, 2009 and which claims priority to Japanese Patent Application Nos. JP 2008-259963 filed on Oct. 6, 2008 and JP 2009-038676 filed on Feb. 20, 2009, the entire contents of which are being incorporated herein by reference.

BACKGROUND

The present disclosure relates to a fuel cell using an oxidoreductase, and an enzyme electrode for use therein.

A fuel cell fixedly provided with an oxidoreductase on an electrode for use as a catalyst (hereinafter, referred to also as enzyme cell) is receiving attention as a next-generation fuel cell with a large capacity and an excellent level of safety. This is because, with such a fuel cell, electrons can be extracted with a good efficiency from a fuel of glucose, ethanol or others that are not available for use as general industrial catalysts.

With an enzyme cell using glucose as a fuel, like a reaction scheme shown in FIG. 27, the oxidation reaction of the glucose (Glucose) takes place at the anode, and at the cathode, the reduction reaction of oxygen (O2) in the air takes place. At the anode, electrons are directed to pass through in order of glucose, glucose dehydrogenase, nicotinamide adeninedinucleotide (NAD+), diaphorase, an electron mediator, and an electrode (carbon). On the other hand, at the cathode, the electrons emitted from the anode are directed to pass through in order of an electrode (carbon), an electron transfer mediator, and bilirubin oxidase (BOD). The reduction reaction is then taken place by these electrons and the oxygen coming from the outside so that electrical energy is generated.

A biological fuel cell exemplified by such an enzyme cell has several problems for practical use thereof. For example, as to any previous biological fuel cell, the power to be produced thereby is smaller than that by any other types of fuel cells. Therefore, in order to obtain the higher power, increasing the capacity of the cell is a requirement as well as configuring the cell like a layer-built cell. In addition, the fuel of the biological fuel cell is generally in the liquid state and is very viscous. There is a possibility of leakage of fuel because the fuel is in the liquid state, although is very viscous. If the container for storage of the fuel is sealed tighter for the purpose of preventing such a fuel leakage, this causes a problem of difficulty in supplying the fuel to the inside of the cell because the fuel is high in viscosity.

In consideration thereof, in recent years, in order to solve such problems related to the biological fuel cell, various studies have been conducted (refer to Patent Literatures 1 and 2). Patent Literature 1 describes a button-shaped biological fuel cell, which includes a cathode, a proton conductor, and an anode that are disposed one on the other in this order. The resulting layer-built structure is sandwiched between a cathode current collector and an anode current collector. The cathode current collector is formed with a supply port of an oxidizing agent, and the anode current collector is formed with a supply port of a fuel. In such a fuel cell, the outer edge of the cathode current collector is caulked to the outer periphery portion of the anode current collector via a gasket to make uniform the pressure to be imposed on the components, and to increase the degree of contact among the components, thereby preventing variations in the power and leakage of the fuel.

Patent Literature 2 describes an enzyme cell, which is aiming to increase the output current or the output voltage by providing a plurality of cell portions in a cell. FIG. 28 shows the configuration of such a previous enzyme cell described in Patent literature 2. This enzyme cell 100 is provided with cell portions 115 and 116. The cell portion 115 is configured by a cathode 103, a proton conductor 104, and an anode 105. The cell portion 116 is configured by an anode 109, a proton conductor 110, and a cathode 111. These cell portions 115 and 116 are disposed with a spacer 107 sandwiched therebetween. In such a manner as to enclose the anodes 105 and 109, the anode current collectors 106 and 108, and the spacer 107, a fuel storage container 114 is provided. To the outside of the cathodes 103 and 111, the cathode current collectors 102 and 112 are respectively disposed, and to the outside thereof, spacers 101 and 103 that can pass therethrough the air are provided.

With such an enzyme cell 100, the anodes 105 and 109 are each fixedly provided with an enzyme, and when the fuel storage container 114 is filled with a glucose solution for use as a fuel, at the anodes 105 and 109, electrons are extracted by the glucose being decomposed by the enzyme, and protons (H+) are generated. At the cathodes 103 and 111, water is generated by the reaction of H+ and the electrons with the oxygen in the air. The H+ are those transported through the proton conductors 110 and 104, and the electrons are those provided via an external circuit after being extracted at the anodes 105 and 109. When a load is connected between the cathode current collectors 102 and 112 and the anode current collector 106, the load is provided therethrough a flow of current being the sum of the output currents of the two cell portions 115 and 116. Thus, the resulting output current and voltage can be larger than those in the previous enzyme cell.

CITATION LIST

Patent Literature

Patent Literature 1: Japanese Unexamined Patent Publication No. 2008-282586

Patent Literature 2: Japanese Unexamined Patent Publication No. 2007-188810

SUMMARY

However, such previous biological fuel cells as described in Patent Literatures 1 and 2 have problems as below because the cathode thereof is in the air-exposing configuration. That is, in the biological fuel cell in such a configuration, the cathode is easily changed in performance capabilities due to the influence of the external environment such as humidity, and this thus causes a problem of power reduction. Moreover, any supplied solution takes time to reach from the anode side to the cathode side, and there thus is a problem of the performance capabilities of initial power generation being low. There is also a problem of easily causing leakage of the solution from the cathode toward the side of air.

Especially when the cell is configured like a layer-built cell for the purpose of increasing the power, the resulting biological fuel cell may be considerably reduced in power in its entirety as is greatly affected by the external environment and the permeability of the solution. In consideration thereof, for the biological fuel cell in the multi-layer cell structure, configuring those to be easy to absorb the solution is important.

Moreover, for disposing one on the other the cells in the air-exposing configuration, leakage of the solution may link together the adjacent cells, thereby possibly causing power reduction of the biological fuel cell in its entirety. There thus needs to dispose the cells with a sufficient space from one another. As such, the biological fuel cell in the air-exposing multi-layer cell structure is complex in structure, and thus has the problem with a low volumetric efficiency.

Also with the previous biological fuel cell, a current collector of the electrode (enzyme electrode) in use is a rolled sheet made of expanded metal. However, this current collector is provided with an enzyme fixing film for use of fixation of enzyme onto the electrode. As a result, the capabilities of current collection from the electrode are reduced, and this causes a problem of power reduction.

An object of the present embodiments is to provide a fuel cell that is high in performance capabilities of initial power generation and in volume power density, and produces a stable power.

A second object of the present embodiments is to provide an enzyme electrode that can increase the power of the fuel cell with an improved configuration of a current collector therein.

A fuel cell an embodiment is provided with a plurality of cells each in which a cathode and an anode are disposed to oppose each other with a proton conductor sandwiched therebetween. In the fuel cell, one or both of the electrodes being the cathode or the anode is fixedly provided with an oxidoreductase for use as a catalyst, and both of the cathode and anode are exposed to a fuel solution.

The fuel cell embodiment is in the water-absorbing multi-layer cell structure in which the cathode is also exposed to the fuel solution. Such a configuration enhances surely not only the performance capabilities of oxygen supply but also the performance capabilities of fuel and electrolytic solution supply, and protects the fuel cell from the influence of the external environment. This accordingly brings a significant increase of the performance capabilities of initial power generation and of the volume power density, and produces a stable power.

An enzyme electrode embodiment is provided with an electrode substrate, an enzyme fixing film for enzyme fixation onto the electrode substrate, and a current collector formed with a convex portion that is higher than the thickness of the enzyme fixing film. The convex portion of the current collector and the electrode substrate come in contact with each other mechanically and electrically with or without a torque generated.

According to the fuel cell embodiment, the water-absorbing multi-layer cell structure is used in which the cathode and anode are both exposed to a fuel solution. This accordingly leads to the high performance capabilities of initial power generation and to the high volume power density, and thus the power can be stabilized.

Moreover, according to the enzyme electrode embodiment, the current collector is provided with the convex portion higher than the thickness of the enzyme fixing film, and via this convex portion, the current collector and the electrode substrate come in contact with each other. This accordingly reduces the contact resistance between the electrode substrate formed with the enzyme fixing film and the current collector so that the power of the resulting fuel cell can be much higher.

Additional features and advantages are described herein, and will be apparent from, the following Detailed Description and the figures.

DETAILED DESCRIPTION

In the below, embodiments are described in detail by referring to the accompanying drawings. The description is given in the following order.

1. First Embodiment (fuel cell having water-absorbing multi-layer cell structure)
2. Second Embodiment (fuel cell having water-absorbing single-layer cell structure)

3. Modified Examples
4. Another Example of Enzyme Electrode (improved electrode current collector)

(1. First Embodiment)

(Entire Configuration)

Figure 1:
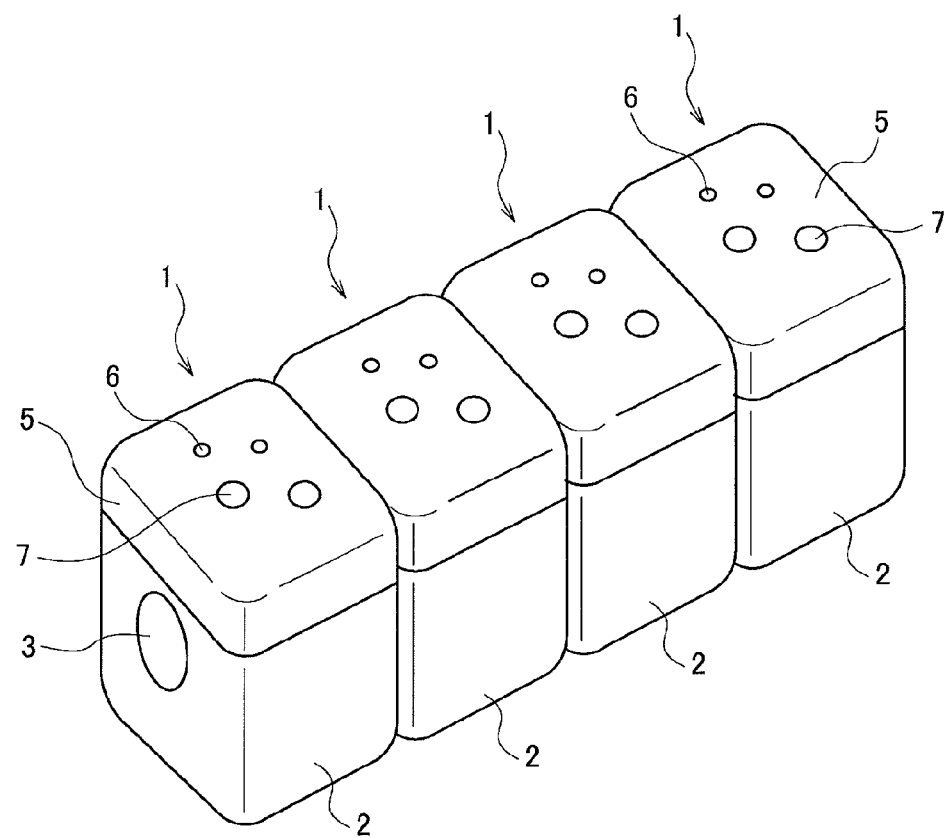
[FIG. 1] A perspective view of fuel cells in a first embodiment, showing the state of use thereof.

First, described is a fuel cell 1 in a first embodiment. FIG. 1 is a schematic view of this fuel cell 1, showing the state of use thereof. In this embodiment, the fuel cell 1 is connected with three others in series, for example. FIGS. 2(A) and (B) each show any two of the fuel cells of FIG. 1, showing the configuration of the connection portion therebetween. FIG. 2(B) is a cross sectional view of the fuel cells of FIG. 2(A), showing the configuration thereof cut along a line A-A. The fuel cell 1 in this embodiment is a biological fuel cell in which an anode and a cathode are each fixedly provided with an oxidoreductase for use as a catalyst, and a container 2 houses therein a battery cell. Note that described herein is an example in which both an anode and a cathode are fixedly provided with an oxidoreductase for use as a catalyst. However, the invention is surely applicable to a case where either the anode or the cathode is fixedly provided with the oxidoreductase.

In this fuel cell 1, the upper portion of the container 2 is formed with an aperture, and on the aperture, an upper lid 5 is disposed. The upper lid 5 is formed with a plurality of holes (fuel supply hole(s) 6, and an exhaust hole(s) 7) for fuel supply or exhaust use. The outer surface of the container 2 is provided with terminals 3 and 4 as shown in FIGS. 1 and 2(A), and these terminals 3 and 4 allow the series or parallel connection of a plurality of fuel cells 1.

(Internal Configuration)

Figure 2:
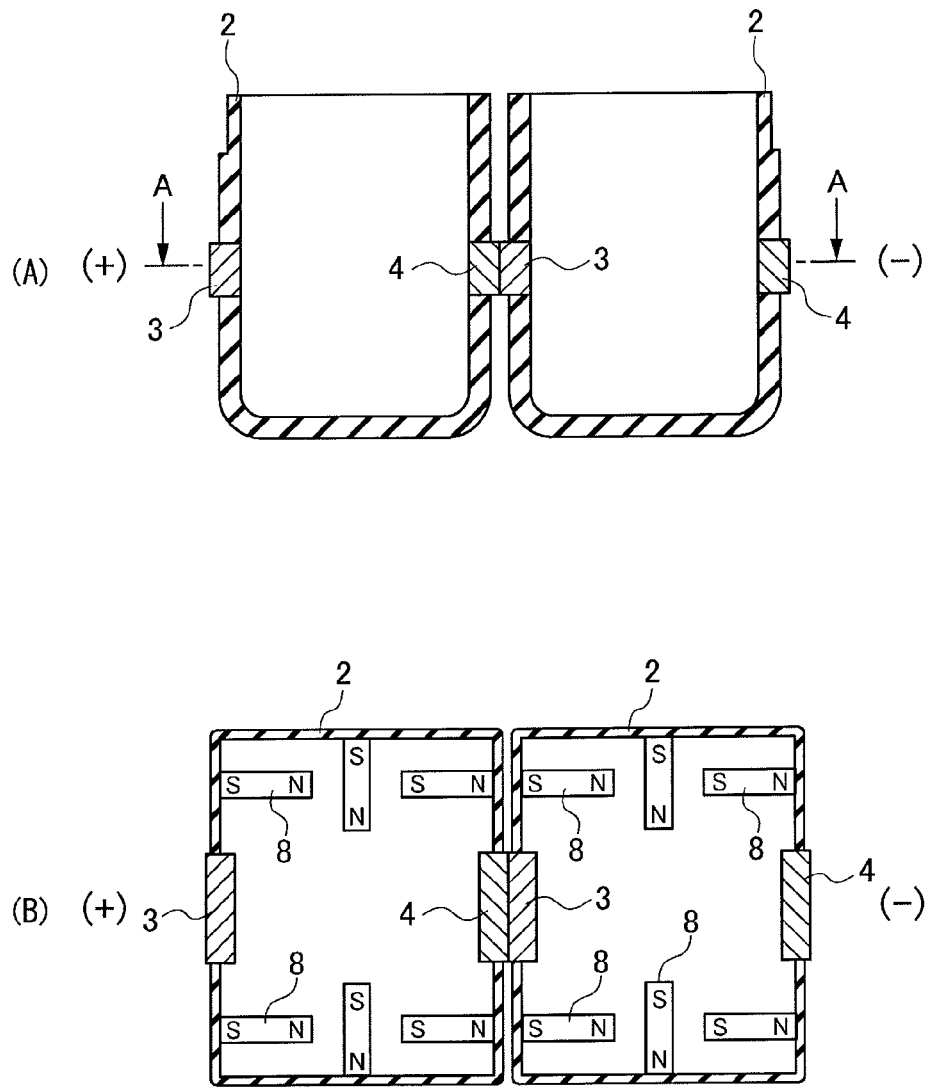
[FIG. 2] A cross sectional view of a connection section between the fuel cells shown in FIG. 1, and (B) is a cross sectional view cut across a line A-A shown in (A).
Figure 3:
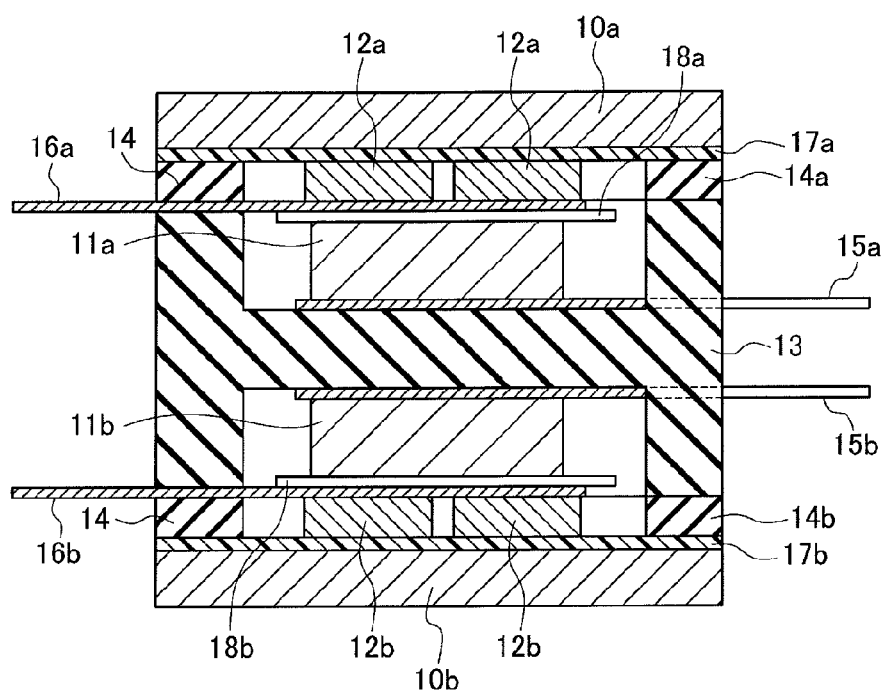
[FIG. 3] A cross sectional view of the fuel cells shown in FIG. 1, showing the internal configuration thereof.

FIG. 3 is a diagram showing the internal configuration of each of the fuel cells 1 shown in FIG. 1. FIG. 3 corresponds to the cross section cut along the line A-A shown in FIG. 2. The fuel cell 1 is provided therein with a plurality of cell portions (single-cell), and the cell portions are each in the water-absorbing multi-layer cell structure in which both the anode and the cathode are exposed to a fuel solution. To be specific, between fixing plates 10a and 10b, first and second cell portions are provided. The first cell portion is configured by an anode 11a, a cathode 12a, and a proton conductor 18b. The second cell portion is configured by an anode 11b, a cathode 12b, and a proton conductor 18b.

The anodes 11a and 11b are disposed so as to oppose each other with an anode spacer 13 sandwiched therebetween. Between the anodes 11a and 11b and the spacer 13, anode current collectors 15a and 15b are respectively provided. Between the proton conductor 18a and the cathode 12a, and between the proton conductor 18b and the cathode 12b, cathode current collectors 16a and 16b are respectively provided. The anode current collectors 15a and 15b, and the cathode current collectors 16a and 16b are respectively connected to the terminals 3 and 4 provided to the side surfaces of the container 2.

The first and second cell portions are connected to each other in parallel. To be specific, via an electrolytic solution stored in the anode spacer 13, the anode 11a in the first cell portion and the anode 11b in the second cell portion are connected to each other, and via the cathode current collectors 16a and 16b, the cathode 12a in the first cell portion and the cathode 12b in the second cell portion are connected to each other.

Around the cathodes 12a and 12b, cathode spacers 14a and 14b are respectively disposed. Between the cathodes 12a and 12b, the cathode spacers 14a and 14b, and the fixing plates 10a and 10b, gas-liquid separation and permeable films 17a and 17b are respectively provided.

In such a fuel cell 1, in a space formed by the gas-liquid separation and permeable films 17a and 17b, the anode spacer 13, and the cathode spacers 14a and 14b, a fuel solution such as glucose solution is filled. In the below, the configuration components in this fuel cell 1 are each described in more detail.

(Anodes 11a and 11b)

The anodes 11a and 11b are each configured by fixedly providing an oxidoreductase on the surface of an electrode made of a conductive porous material. In these anodes 11a and 11b, the enzyme fixedly provided on the surface decomposes the fuel, thereby extracting electrons and producing protons (H+). For the conductive porous material configuring these anodes 11a and 11b, any well-known material can be used, but especially a carbon material is suitable such as porous carbon, carbon pellet, carbon felt, carbon paper, carbon fiber, or carbon-particle laminate. For the enzyme to be fixedly provided on the surfaces of the anodes 11a and 11b, when a fuel is glucose, for example, possibly used is a glucose dehydrogenase (GDH) for decomposition of the glucose.

When the fuel in use are monosaccharides such as glucose, the anodes 11a and 11b are desirably provided fixedly on the surfaces with a coenzyme oxidase or an electron mediator together with an oxidase, which speeds up the oxidation of monosaccharides such as GDH before decomposition thereof. The coenzyme oxidase is for the oxidation of a coenzyme to be reduced by an oxidase (e.g., NAD+, and NADP+) and of a reductant of the coenzyme (e.g., NADH, and NADPH), and is exemplified by diaphorase. Due to the action of such a coenzyme oxidase, electrons are generated when the coenzyme is changed in form again to the oxidant, and the electrons are provided by the coenzyme oxidase to the electrode via an electron mediator.

The electron mediator for use is preferably a quinone-skeleton compound, and especially a naphthoquinone-skeleton compound is suitable. To be specific, possible options include 2-amino-1,4-naphthoquinone (ANQ), 2-amino-3-methyl-1,4-naphthoquinone (AMNQ), 2-methyl-1,4-naphthoquinone (VK3), 2-amino-3-carboxy-1,4-naphthoquinone (ACNQ), and others. As the quinone-skeleton compound, other than the naphthoquinone-skeleton compound, anthraquinone or a derivative thereof is also a possibility. Also, as required, one or more other types of compounds each acting as an electron mediator may be fixedly provided together with the quinone-skeleton compound.

When the fuel in use are polysaccharides, in addition to the oxidase, the coenzyme oxidase, the coenzyme, and the electron mediator, desirably, a decomposition enzyme is fixedly provided for speeding up the decomposition such as hydrolysis of polysaccharides, and producing monosaccharides such as glucose. Note here that the term of "polysaccharides" denotes "polysaccharides" in a broad sense, indicates every carbohydrate producing two or more monosaccharide molecules by the hydrolysis, and includes oligosaccharides such as disaccharide, trisaccharide, and tetrasaccharide. To be specific, examples include starch, amylose, amylopectin, glycogen, cellulose, maltose, sucrose, and lactose. These are the bonding results of two or more types of monosaccharides, and in whatever polysaccharides, the glucose is included as a monosaccharide being a bonding unit.

Moreover, the amylose and amylopectin are each a component included in starch, and the starch is a mixture of the amylose and amylopectin. When the decomposition enzyme for the polysaccharides is glucoamylase, and when the oxidase for decomposing the monosaccharides is glucose dehydrogenase, for example, the fuel in use can be polysaccharides, which can be decomposed further into glucose by the glucoamylase. Such polysaccharides are exemplified by starch, amylose, amylopectin, glycogen, and maltose. Herein, the glucoamylase is a decomposition enzyme for the hydrolysis of α-glucan such as starch, and for producing glucose. The glucose dehydrogenase is an oxidase for the oxidation of β-D-glucose to D-glucono-δ-lactone.

(Cathodes 12a and 12b)

The cathodes 12a and 12b are each configured by fixedly providing an oxidoreductase and an electron mediator on the surface of an electrode made of a conductive porous material. In these cathodes 12a and 12b, water is generated by protons, electrons, and oxygen in the air, for example. The protons are those provided by the anodes 11a and 11b through the proton conductors 18a and 18b, and the electrons are those provided by the anodes 11a and 11b via an external circuit. For the conductive porous material configuring the cathodes 12a and 12b, any well-known material can be used, but especially a carbon material is suitable such as porous carbon, carbon pellet, carbon felt, carbon paper, carbon fiber, or carbon-particle laminate.

The oxidoreductase to be fixedly provided to the cathodes 12a and 12b is exemplified by bilirubin oxidase, laccase, and ascorbate oxidase. The electron mediator for fixation together with such enzymes is exemplified by potassium ferrocyanide, potassium ferricyanide, and potassium octacyanotungstate.

In the fuel cell 1 in the embodiment, desirably, the cathodes 12a and 12b are made water-repellent at least partially on the surfaces. If this is the configuration, the moisture content of the resulting cathodes 12a and 12b can remain in an optimum range, and with such cathodes 12a and 12b, a catalyst current value can be extremely high. Herein, the electrode surfaces of the anodes 11a and 11b and those of the cathodes 12a and 12b each include entirely the outer electrode surface and the inner surface of the cavity inside of the electrode.

For making partially water-repellent on the surfaces of the cathodes 12a and 12b, a possible method is to apply a water repellent on the surfaces of the cathodes 12a and 12b, or to soak the cathodes 12a and 12b in the water repellent. The water repellent for use thereto may be of various types, but the suitable one is a fine-grained water repellent material being dispersed in an organic solvent. The organic solvent in the water repellent desirably has a sufficiently low enzyme solubility, e.g., the solubility of 10 mg/ml or lower, and preferably, 1 mg/ml or lower.

Alternatively, the water repellent may contain a binder resin such as polyvinyl butyral. The binder resin in the water repellent is 0.01 to 10 mass %, but this is surely not restrictive. Moreover, when the binder resin is a material with water repellency such as PVDF, the binder resin itself may be used as a water repellent material. The water repellent material for use can be of various types, and examples include a carbon material, and suitably carbon powder. The carbon powder includes graphite such as natural graphite, activated carbon, carbon nanofiber (vapor-phase grown carbon fiber), and Ketjen black, for example.

Figure 4:
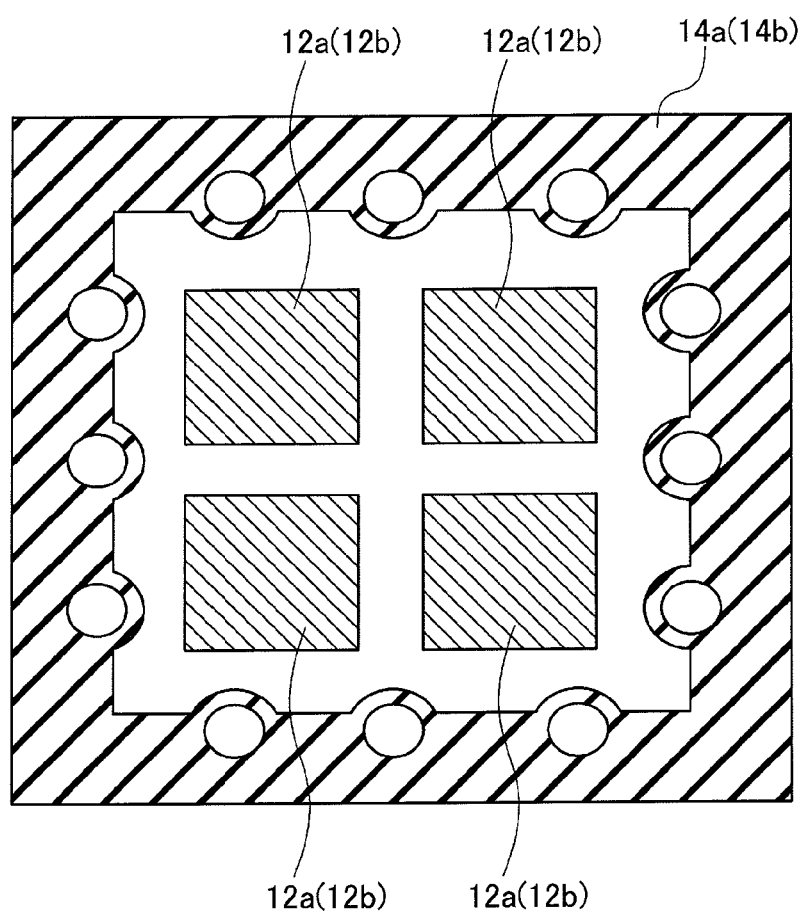
[FIG. 4] A plan view of cathodes shown in FIG. 3, showing the configuration thereof.

FIG. 4 is a diagram showing the configuration of the cathodes 12a and 12b of FIG. 3 in planar view. In the fuel cell 1 in this embodiment, the cathodes 12a and 12b are each divided into a plurality of pieces for placement, and the electrodes are each disposed with a space from others. Such a space between the electrodes helps replacement of air with a fuel solution, thereby being able to provide swiftly the fuel solution into the cell. This accordingly improves the performance capabilities of the initial power generation, thereby allowing power generation with a high degree of efficiency immediately after the supply of a fuel and an electrolytic solution.

In the fuel cell 1 in the embodiment, the cathodes 12a and 12b are each divided into four pieces, but the dividing number is surely not restrictive thereto, and is arbitrarily determined. Furthermore, the cathodes 12a and 12b are each not necessarily divided into pieces for placement. Alternatively, a through hole may be formed at the center portion of each thereof possibly for the passage of a fuel solution, or a plurality of minute holes may be provided possibly for the passage of the fuel solution by a capillary phenomenon.

(Cathode Spacers 14a and 14b)

As shown in FIG. 4, in the fuel cell 1 in this embodiment, the cathode spacers 14a and 14b are disposed around the cathodes 12a and 12b. These cathode spacers 14a and 14b are each a sealing member for use to prevent leakage of air and the fuel solution in the cell, and are each made of a high-density plastic material such as silicone resin and PTFE (polytetrafluoroethylene) not allowing the passage of gas and liquid therethrough. The cathode spacers 14a and 14b are each filled therein with the fuel solution. These cathode spacers 14a and 14b may be each formed with a plurality of holes for fixation to the anode spacer 13, for example.

(Proton Conductors 18a and 18b)

The proton conductors 18a and 18b are those respectively for transporting the protons (H+) produced in the anodes 11a and 11b to the cathodes 12a and 12b, and are each made of a material that is not electronically conductive, and is capable of transporting the protons (H+) as such. For the material with such characteristics, exemplified are cellophane, gelatin, and an ion-exchange resin including fluorine-containing carbon sulfonic acid groups. The proton conductors 18a and 18b can be also made of an electrolyte material. If this is the case, any nonwoven fabric or others may be used as a separator, and this separator may be soaked in the electrolyte material so that the resulting separator can be incorporated easily in the fuel cell.

(Anode Spacer 13)

The anode spacer 13 is formed with a plurality of through holes (not shown) in the plane direction to allow the passage of a fuel and an electrolytic solution therethrough. The end portions of this anode spacer 13 both function as sealing members for preventing leakage of a fuel solution. In the fuel cell 1 in this embodiment, this anode spacer 13 serves also as a fuel tank for storage of the fuel. Such an anode spacer 13 will do as long as it is insulative, and may be made of a hard plastic material such as acrylic resin, for example.

(Gas-Liquid Separation and Permeable Films 17a and 17b)

The gas-liquid separation and permeable films 17a and 17b are each a film not allowing the passage of liquid therethrough but only gas, and each allow the passage of air (oxygen) therethrough while preventing leakage of the fuel solution. Such gas-liquid separation and permeable films 17a and 17b may be each a film made of polyvinylidine difluoride (PVDF) and PTFE, or a porous film being the result of coating of PVDF or PTFE on the surface, for example. The gas-liquid separation and permeable films 17a and 17b are surely not restrictive thereto, and any well-known films may be used as appropriately selected.

(Fixing Plates 10a and 10b)

The fixing plates 10a and 10b are for fixedly positioning the components by sandwiching those components from both sides. These fixing plates 10a and 10b are each made of a hard material such as aluminum plate anodized on the surface. The fixing plates 10a and 10b are each formed with a plurality of through holes (not shown) in the plane direction to allow the passage of air (oxygen) therethrough.

(Method of Connection)

The fuel cell 1 in this embodiment can be connected to other fuel cell(s) 1. As shown in FIG. 2(B), for example, one method of connection is to dispose one or more magnets 8 on the inner side surfaces of the container 2, and by the magnetic force thereof, the fuel cells 1 are pulled to be closer to each other so that the terminals 3 and 4 come in contact with each other. In this configuration, the magnet(s) 8 will do as long as they are disposed so as to be able to bring closer together the positive terminal 3 and the negative terminal 4. FIG. 2 shows the configuration in which only the terminals 3 and 4 are in contact, and the containers 2 are disposed with a space therebetween. The containers 2 may be also in contact as are the terminals 3 and 4.

Figure 5:
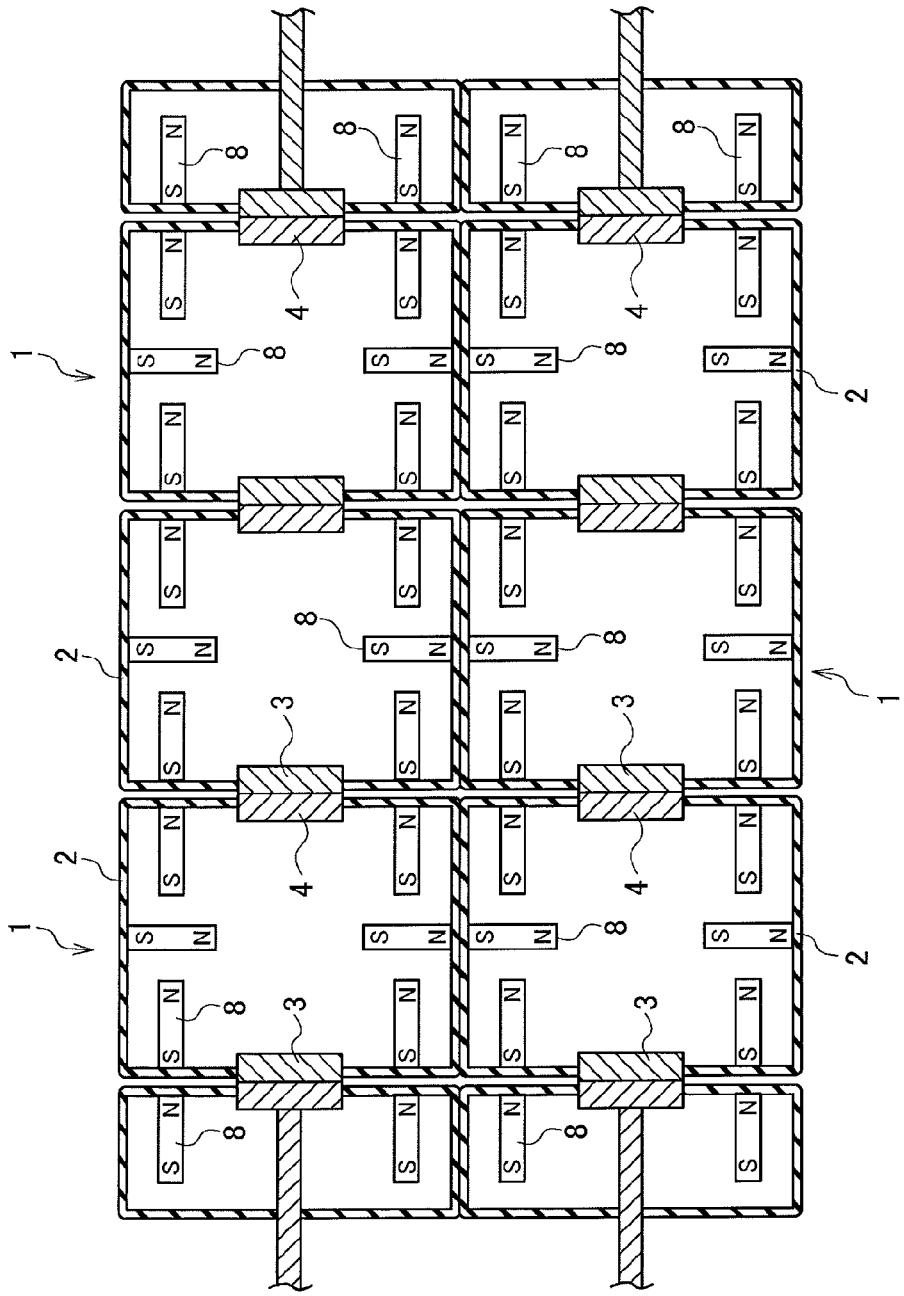
[FIG. 5] A perspective view of the fuel cells shown in FIG. 1, showing another state of connection thereamong.

FIG. 5 is a diagram showing another state of connection for the fuel cells 1. The side surfaces not provided with the terminals 3 and 4 in each of the containers 2 are also provided with the magnet(s) 8 so that any of the not-connected fuel cells 1 can be disposed adjacent to each other. By establishing a connection between the terminals 3 and 4 by the magnetic force as such, any erroneous connection can be prevented, and the fuel cells 1 can be connected self-organizingly in a quick and easy manner. With such a method of connection, the terminals 3 and 4 are only being in contact with each other. Accordingly, even if any one of the connected fuel cells 1 is put under the external force, the fuel cell can be easily disconnected from others without causing damages to the terminals 3 and 4, and any other components. Moreover, disposing the magnets 8 based on the layout combination of S and N poles allows positioning of the fuel cells 1.

(Method of Fuel Supply)

In this fuel cell 1, the container 2 is formed with, on the upper surface, the fuel supply hole(s) 6, and the exhaust hole(s) 7. The fuel supply hole(s) 6 are each for refilling a liquid fuel such as glucose and ethanol to the cell portions, and the exhaust hole(s) 7 are each for preventing any pressure increase in the container 2 by releasing the air therein to the outside. The fuel supply hole(s) 6 and the exhaust hole(s) 7 are all preferably as small as possible to keep the fuel storage container airtight. If they are, a syringe or others may be used for easy filling of a fuel. Also for preventing leakage of the fuel solution together with the gas in the tank to the outside of the container, the exhaust hole(s) 7 are each preferably provided with a liquid pool.

Such a fuel cell 1 allows filling of a fuel from the above, but alternatively, may be provided with a fuel filling portion for filling the fuel provided through the fuel supply hole(s) 6 at a predetermined position in the fuel tank and/or in a predetermined direction. As a possible specific configuration, a tube may be disposed inside of the fuel tank for filling of the fuel from beneath the electrode. This allows to release the air in the fuel tank to the outside with a good efficiency, and thus a good amount of fuel can reach inside of the tank, and also any gas (e.g., $CO_2$) generated by the reaction is expected to be pushed upward in the fuel tank for emission. Alternatively, the inner space of the fuel tank may be configured like capillary, and the fuel may be filled therein by utilizing a capillary phenomenon. If this is the configuration, the fuel can be directed to inside of the fuel tank from the outside thereof with no pressure and no flow change.

(Effects)

As such, the fuel cell 1 in the embodiment is in the water-absorbing cell structure in which both the anode and the cathode are exposed to a fuel solution. This improves not only the supply performance of oxygen but also the supply performance of fuel and electrolytic solution, and the resulting fuel cell is not susceptible any more to any influence of the external environment. As a result, the performance capabilities of initial power generation are improved, and the power is stabilized. Moreover, this configuration allows a plurality of cells to share a fuel tank so that there is no more need to provide a gasket to each tank for prevention of leakage. This thus favorably increases the volume power density, and reduces the capacity.

Also in the fuel cell 1 in this embodiment, the cathodes 12*a* and 12*b* are each divided into pieces for placement for the smoother passage of a fuel solution, thereby obtaining the satisfactory supply performance of fuel, and improving the initial power to a further degree. Also in the fuel cell 1 in this embodiment, the outer side surface of the container 2 is provided with the positive terminal 3 and the negative terminal 4 for connection use with other fuel cells, and this configuration thus achieves easy connection among a plurality of fuel cells. Accordingly, when one fuel cell is not enough in terms of power, by simply coupling the fuel cell to another, a higher power can be obtained in a quick and easy manner.

Also in the fuel cell 1 in the embodiment, the fuel supply hole(s) 6 and the air exhaust hole(s) 7 are formed to the surface not provided with the terminals 3 and 4. This helps to increase the coupling degree between the fuel cells, and after the fuel cells are coupled together, a fuel can be filled into the battery cells with a good efficiency. As a result, the fuel supply can be completed in a shorter length of time, and the initial power can be increased to a further degree.

Note that, in this embodiment, exemplified is the multilayer cell in which two cell portions are connected in parallel. The invention is surely not restrictive thereto, and is applicable also to a layer-built cell of various configurations in which a plurality of single cells are connected in parallel and/or in series. For connecting a plurality of fuel cells, the serial connection is surely not the only option, and a plurality of fuel cells may be connected also in parallel. If this is the configuration, the positive and negative terminals may be disposed on any other surface. In other words, the number and the position of the terminals in the fuel cell can be changed as appropriate depending on the state of connection.

Similarly, as long as being formed to the surface not provided with the terminals, the fuel supply hole(s) and the exhaust hole(s) may be also changed as appropriate in number and position based on the use of the fuel cell, the state of connection thereof, and the battery cells therein. In an exemplary configuration, the positive and negative terminals may be disposed on both the upper and lower surfaces, and a plurality of fuel cells may be connected as if piling those up in the vertical direction. If this is the configuration, the fuel supply hole(s) and the exhaust hole(s) may be formed to either of the side surfaces.

Moreover, the method of connection for the terminals is also surely not restricted to the method of using the magnetic force, and alternatively, the positive terminal 3 may be shaped like a convex, and the negative terminal 4 may be shaped like a concave, for example. If this is the case, the positive terminal 3 may be engaged to the negative terminal 4 of any other fuel cell 1, thereby being able to connect together the fuel cells 1 easily. Still alternatively, the positive terminal 3 may be shaped like a male screw, and the negative terminal 4 may be shaped like a female screw for spiral insertion of the positive terminal 3 into the negative terminal 4.

(2. Second Embodiment)

(Entire Configuration)

Figure 6:
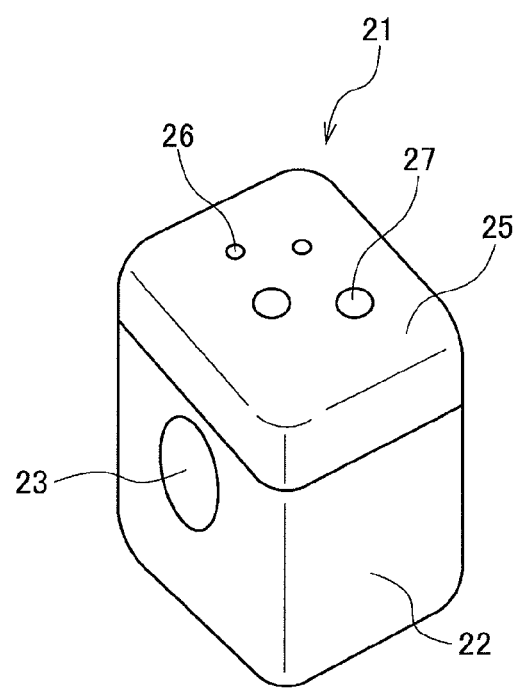
[FIG. 6] A perspective view of a fuel cell in a second embodiment.
Figure 7:
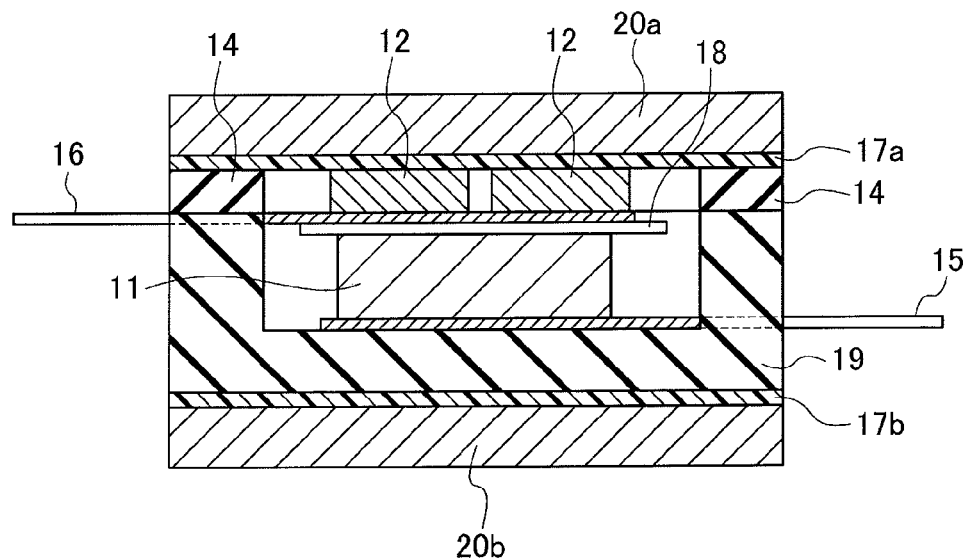
[FIG. 7] A cross sectional view of the fuel cell shown in FIG. 6, showing the internal configuration thereof.

Described next is a fuel cell in a second embodiment. FIG. 6 is a diagram schematically showing a fuel cell 21 in this embodiment, and FIG. 7 shows the internal configuration thereof. The fuel cell 21 in this embodiment is a biological fuel cell in which one or both of electrodes being an anode or a cathode is fixedly provided with an oxidoreductase for use as a catalyst, and a container 22 houses therein a battery cell being a cell portion. Also in such a fuel cell 21, similarly to the first embodiment, the upper portion of the container 22 is formed with an aperture, and on the aperture, an upper lid 25 is disposed. The upper lid 25 is formed with a plurality of holes (a fuel supply hole(s) 26, and an exhaust hole(s) 27) for fuel supply or exhaust use. The outer side surface of the container 22 is provided with terminals, and these terminals allow the series or parallel connection of a plurality of fuel cells 21.

(Internal Configuration)

This fuel cell 21 is provided therein with a cell portion between fixing plates 20a and 20b. The cell portion is configured by an anode 11, a cathode 12, and a proton conductor 18. To be specific, between the fixing plates 20a and 20b, provided in order are a gas-liquid separation and permeable film 17a, the cathode 12, a cathode current collector 16, the proton conductor 18, the anode 11, an anode current collector 15, an anode spacer 19, and a gas-liquid separation and permeable film 17b.

Similarly to the cathodes 12a and 12b shown in FIG. 4, the cathode 12 is divided into a plurality of pieces for placement, and a cathode spacer 14 is disposed therearound. The fixing plate 20a on the side of the cathode 12 is formed with a plurality of through holes (not shown) in the plane direction to allow the passage of air (oxygen) therethrough. The fixing plate 20b on the side of the anode 11 is not necessarily formed with such through holes. Also in such a fuel cell 21, the anode current collector 15 and the cathode current collector 16 are connected to the terminals provided on the side surface of the container 22, respectively. In the fuel cell 21 in this embodiment, a fuel solution is filled into a space formed by the gas-liquid separation and permeable films 17a and 17b, the anode spacer 13, and the cathode spacer 14. In other words, this fuel cell 21 has the water-absorbing single cell structure in which both the anode 11 and the cathode 12 are exposed to a fuel solution.

(Effects)

Since the fuel cell 21 in this embodiment is also in the water-absorbing structure in which the cathode is also exposed to a fuel solution, the fuel cell 21 is not susceptible any more to the influence of the external environment, and the stable power can be obtained. Also since the cathode 12 is divided into a plurality of pieces for placement for the better passage of the fuel solution, the resulting supply performance of fuel becomes satisfactory, and the initial power is improved. Further, since the outer side surface of the container 2 is provided with the positive terminal 3 and the negative terminal 4 for connection use with other fuel cells, and this configuration thus achieves easy connection among a plurality of fuel cells, and obtains a high power in a quick and easy manner. Still further, in this fuel cell 21, the fuel supply hole(s) 26 and the air exhaust hole(s) 27 are disposed on the surface not provided with the terminals for connection use as such, the fuel cells can be coupled together with a higher coupling degree.

In the fuel cell 21 in this embodiment, the remaining configuration and effects not described above are the same as those in the fuel cell 1 in the first embodiment.

(Modified Example)

Figure 8:
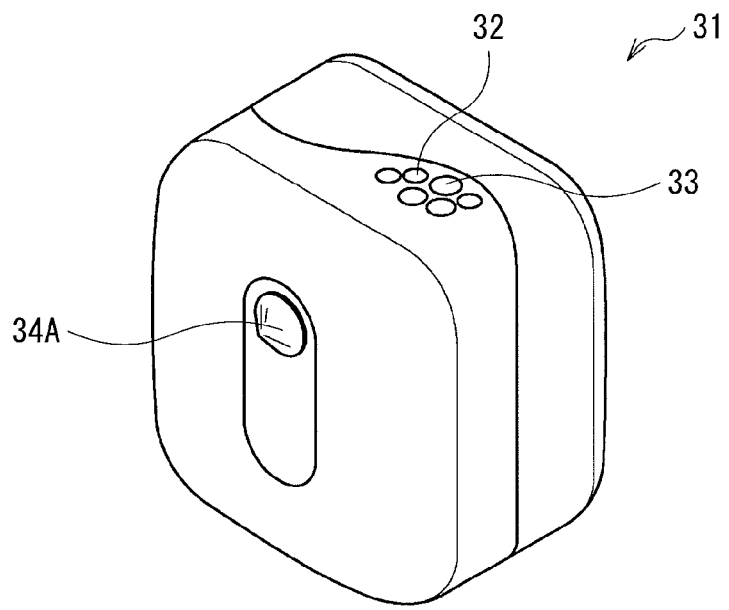
[FIG. 8] A perspective view of a fuel cell in a modified example.
Figure 9:
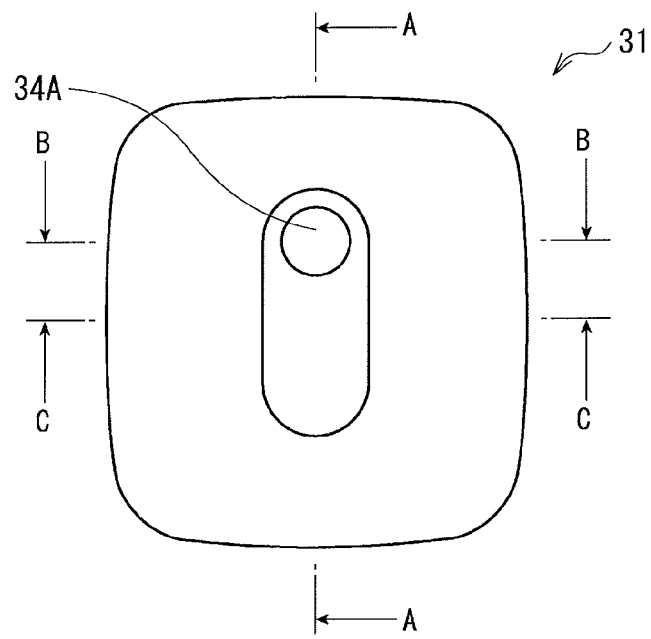
[FIG. 9] A front view of the fuel cell shown in FIG. 8.
Figure 10:
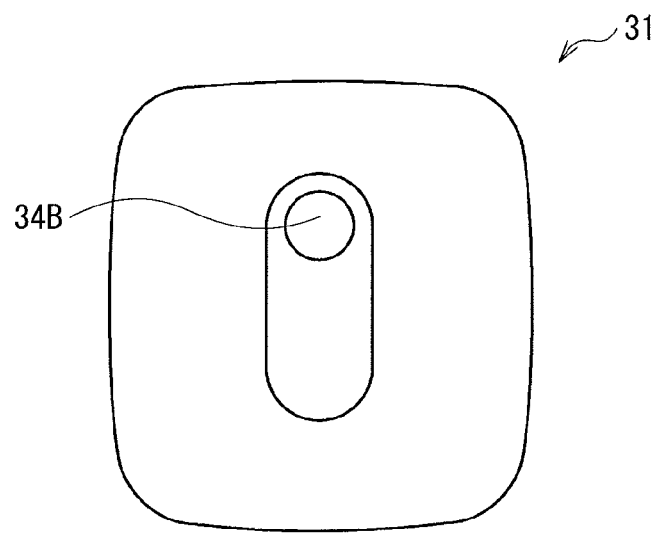
[FIG. 10] A rear view of the fuel cell also in FIG. 8.
Figure 11:
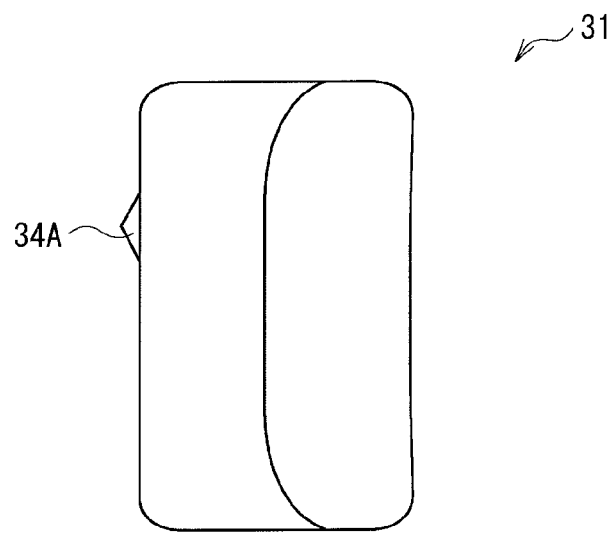
[FIG. 11] A right side view of the fuel cell also in FIG. 8.
Figure 12:
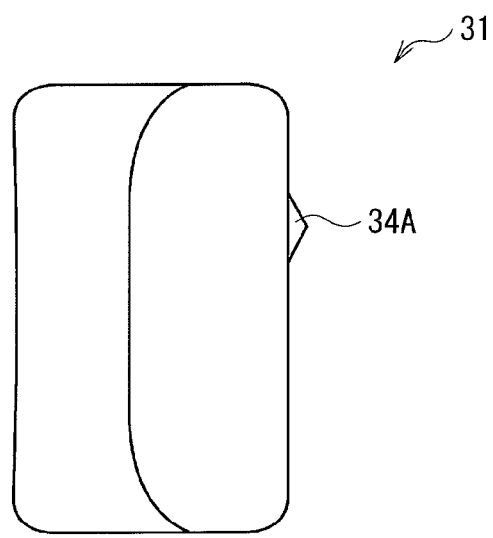
[FIG. 12] A left side view of the fuel cell also in FIG. 8.
Figure 13:
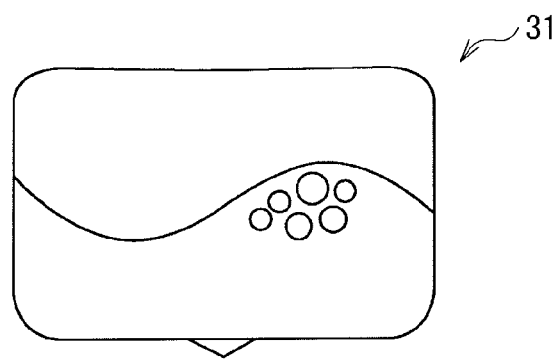
[FIG. 13] An upper view of the fuel cell also in FIG. 8.
Figure 14:
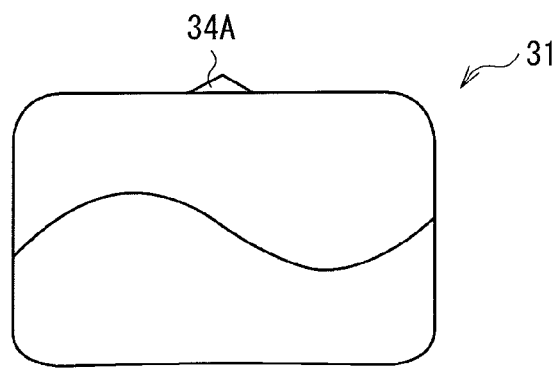
[FIG. 14] A bottom view of the fuel cell also in FIG. 8.
Figure 15:
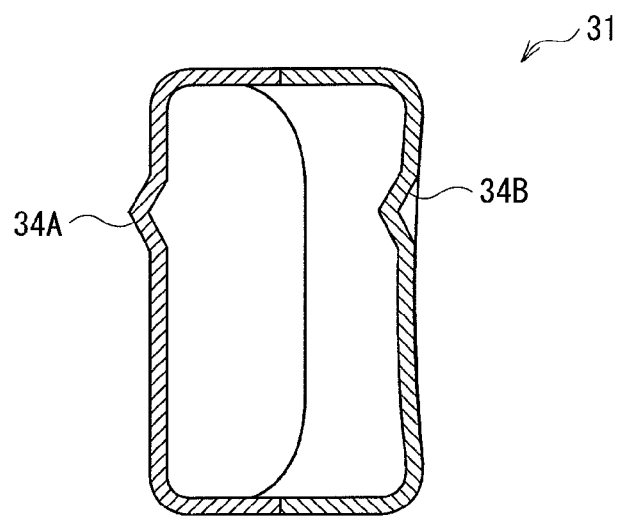
[FIG. 15] A cross sectional view of the fuel cell cut across a line A-A shown in FIG. 9.
Figure 16:
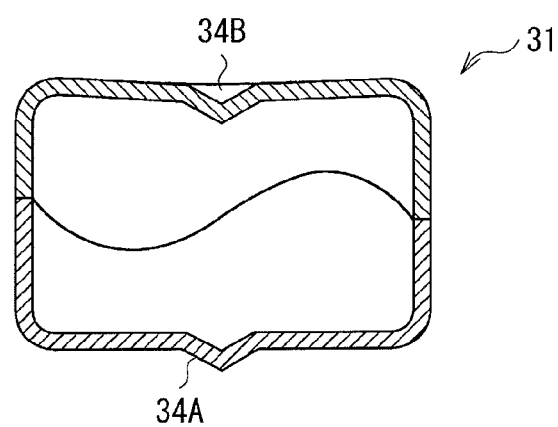
[FIG. 16] A cross sectional view of the fuel cell cut across a line B-B also in FIG. 9.
Figure 17:
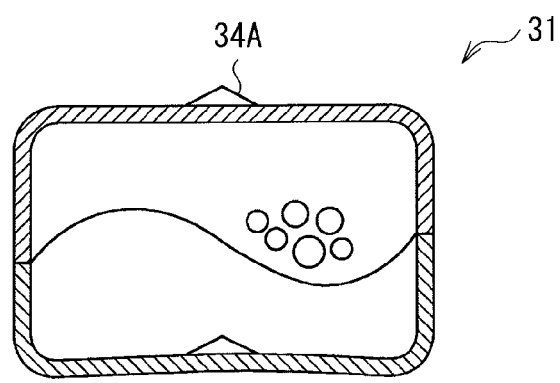
[FIG. 17] A cross sectional view of the fuel cell cut across a line C-C also in FIG. 9.

A fuel cell 31 in a modified example of FIG. 8, an upper lid may not be provided, and a fuel supply hole(s) 32 and an exhaust hole(s) 33 may be collectively disposed at any arbitrary position. Moreover, the terminals may be each arbitrarily shaped, e.g., a conical terminal 34A and an inverted-conical terminal 34B. FIG. 9 is a front view of this fuel cell 31, FIG. 10 is a rear view thereof, FIG. 11 is a right side view thereof, FIG. 12 is a left side view thereof, FIG. 13 is a top view thereof, and FIG. 14 is a bottom view thereof. FIG. 15 is a cross sectional view thereof cut across a line A-A in FIG. 9, FIG. 16 is a cross sectional view thereof cut across a line B-B therein, and FIG. 17 is a cross sectional view thereof cut across a line C-C therein.

Moreover, the fuel cell can be in the shape of a coin or a tube. With a coin-shaped biological fuel cell in an exemplary configuration, one or more cell portions may be disposed between anode current collector and cathode current collector each serving also as a chassis, and the anode and cathode in each of the cell portions are to be exposed to a fuel solution, for example. If this is the configuration, desirably, the cathode current collector is formed with a plurality of through holes for the passage of air (oxygen), and a gas-liquid separation and permeable film is provided between the cathode current collector and the cathode to prevent leakage of a fuel solution. Also in such a coin-shaped biological fuel cell, desirably, the cathode is divided into a plurality of pieces for placement for the better passage of the fuel solution.

With a tube-shaped fuel cell, as in a possible configuration, the anode current collector may be provided therearound with one or more cell portions each including an anode, a proton conductor, and a cathode, and a tubular cathode current collector may be disposed to the outermost portion to expose the anode and the cathode in each of the cell portions to a fuel solution. Also in such a configuration, desirably, the cathode current collector may be formed with a plurality of through holes for the passage of air (oxygen), and a gas-liquid separation and permeable film is provided between the cathode current collector and the cathode to prevent leakage of the fuel solution. Also in such a tube-shaped biological fuel cell, desirably, the cathode is divided into a plurality of pieces for placement for the better passage of the fuel solution.

As such, described above is the fuel cell having the water-absorbing multi-layer cell structure, and described next is an electrode (enzyme electrode) that can increase more the power of such a fuel cell. This enzyme electrode is the structure-improved version of a current collector in the electrodes each being an anode or a cathode, and using such an enzyme electrode, the capabilities of current collection from the electrodes can be enhanced, and the resulting fuel cell can be increased in power. Note that the enzyme electrode described below is suitable for use in the fuel cell having the water-absorbing multi-layer cell structure, but is also applicable to fuel cells in any other different configurations as will be described later.

(Enzyme Electrode)

Figure 18:
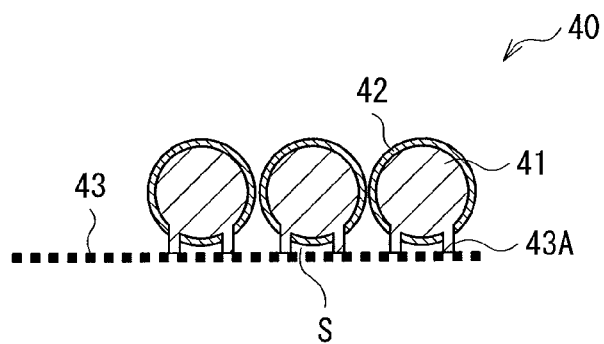
[FIG. 18] A cross sectional view of an enzyme electrode in a modified example.

FIG. 18 is a diagram showing such an enzyme electrode 40, and this enzyme electrode 40 is configured to include an electrode substrate 41, an enzyme fixing film 42, and a current collector 43. In the below, the configuration, function, effects, and others are described for each of such components.

(1. Electrode Substrate 41)

In the electrode substrate 41, the oxidation-reduction reaction takes place with an enzyme used as a catalyst. To be more specific, when this enzyme electrode 40 is used as an anode, a fuel undergoes oxidation on the electrode substrate 41 so that electrodes are emitted. When the enzyme electrode 40 is used as a cathode, a reduction reaction takes place using electrons and oxygen. The electrons are provided through the current collector 43 after being emitted by the anode, and the oxygen is provided from the outside.

The material for the electrode substrate 41 is not specifically restrictive as long as it can establish an electrical connection with the outside, and any well-known raw materials can be freely selected for use therefor. The materials available for use are, for example, metal such as Pt, Ag, Au, Ru, Rh, Os, Nb, Mo, In, Ir, Zn, Mn, Fe, Co, Ti, V, Cr, Pd, Re, Ta, W, Zr, Ge, and Hf, alloys such as Alumel, brass, Duralumin, bronze, nickelin, platinum-rhodium, Hiperco, permalloy, permendur, nickel silver, and phosphor bronze, conductive polymer such as polyacethylene, a carbon material such as graphite and carbon black, boride such as $HfB_2$, $NbB$, $CrB_2$, and $B_4C$, nitride such as $TiN$ and $ZrN$, silicide such as $VSi_2$, $NbSi_2$, $MoSi_2$, and $TaSi_2$, and a material being the combination thereof (2. Enzyme Fixing Film 42)

The enzyme fixing film 42 is a film for use to fixedly provide the enzyme on the electrode substrate 41.

The enzyme to be fixedly provided on the enzyme fixing film 42 as such is not specifically restrictive, and one or more types of enzymes available for use in a biological fuel cell may be freely selected for use. When this enzyme electrode 40 is used as an anode, for example, an oxidase may be fixedly provided. Such an oxidase includes alcohol dehydrogenase, aldehyde reductase, aldehyde dehydrogenase, lactate dehydrogenase, hydroxy pyruvate reductase, glycerate dehydrogenase, formate dehydrogenase, fructose dehydrogenase, galactose dehydrogenase, glucose dehydrogenase, gluconate-5 dehydrogenase, and gluconate-2 dehydrogenase, for example.

The enzyme fixing film 42 may be fixedly provided not only with the oxidase described above but also with oxidized coenzyme and coenzyme oxidase. The oxidized coenzyme includes nicotinamide adeninedinucleotide (hereinafter referred to as "$NAD^+$"), nicotinamide adeninedinucleotide phosphate (referred to as "$NADP^+$"), flavin adeninedinucleotide (hereinafter referred to as "$FAD^+$"), and pyrrolo-quinoline quinone (hereinafter, referred to as "$PQQ2^+$", for example). The coenzyme oxidase is exemplified by diaphorase.

The enzyme fixing film 42 may be fixed not only with the oxidase and the oxidized coenzyme described above but also with an electron transfer mediator. This is for the smooth passing of electrons to the electrode. The electron transfer mediator is exemplified by a naphthoquinone-skeleton compound such as 2-amino-3-carboxy-1,4-naphthoquinone (ACNQ), vitamin K3, 2-amino-1,4-naphthoquinone (ANQ), 2-amino-3-methyl-1,4-naphthoquinone (AMNQ), and 2,3-diamino-1,4-naphthoquinone, a metal complex such as osmium (Os), ruthenium (Ru), iron (Fe), and cobalt (Co), a viologen compound such as benzyl viologen, a chinone-skeleton compound, an anthraquinone-skeleton compound, a nicotinamide-structure compound, a riboflavin-structure compound, and a nucleotide-phosphoric acid-structure compound.

Also when such an enzyme electrode 40 is used as a cathode, possibly used for fixation is an enzyme exhibiting oxidase activity with a reaction substrate of oxygen. Such an enzyme includes laccase, bilirubin oxidase, and ascorbate oxidase, for example.

In addition to such an enzyme as described above, an electron transfer mediator may be fixedly provided. This is for the smooth passing of electrons. The electron transfer mediator available for fixation is not specifically restricted in type, and may be freely selected in type as required. An exemplary mediator for use can be ABTS (2,2'-azinobis(3-ethylbenzoline-6-sulfonate)), $K_3[Fe(CN)_6]$, and others.

A method for forming the enzyme fixing film 42 is not specifically restrictive, and the film can be formed based on a method for forming an enzyme fixing electrode for use in a general biological fuel cell. For example, first of all, the electrode substrate 41 is coated with a conductive coating and then is dried, and the surface of the resulting electrode substrate 41 then undergoes a process of ozone cleaning. Thereafter, the resulting structure is coated with a solution including the enzyme, the coenzyme, the electron transfer mediator, and others described above, and then is dried. An aqueous solution of the materials for fixation, e.g., poly-L-lysine (PLL) and polyacrylic acid (PAAc), is then coated on the resulting structure, and then is dried. In this manner, the enzyme fixing film 42 can be formed.

The enzyme fixing film 42 is not specifically restricted in thickness as long as an enzyme or others can be fixedly provided thereon, but the thickness is preferably 40 to 80 µm.

(3. Current Collector 43)

The current collector 43 is connected to an external circuit, and is in charge of directing the electrons emitted by the anode toward the cathode via the external circuit. This current collector 43 is formed with a convex portion 43A, and by this convex portion 43A, the current collector 43 and the electrode substrate 41 come in contact with each other. This accordingly extremely enhances the capabilities of the current collector 43 for current collection from the electrode substrate 41, thereby realizing a high output of the resulting electric energy.

Note that the expression of "convex portion" in this specification includes any portion as long as it is in the convex shape, e.g., spike-shaped, needle-shaped, cylinder-shaped, prism-shaped, cone-shaped, and geometrical pyramid-shaped, and also includes any portion in the convex shape with the current collector 43 being wave-shaped, mountain-shaped, valley-shaped, and others.

The height of the convex portion 43A from the surface of the current collector 43 is set so as to be higher than the thickness of the enzyme fixing film 42 to be in contact with the electrode substrate 41. The specific height thereof can be set freely in accordance with the thickness of the enzyme fixing film 42, and is preferably 0.1 to 1.0 mm. This is to be in contact with the electrode substrate 41 without fail.

Also preferably, by setting the convex portion 43A to be higher than the thickness of the enzyme fixing film 42, a cavity S is formed without fail between the current collector 43 and the enzyme fixing film 42. This cavity S allows the smooth supply of substance such as fuel between the current collector 43 and the enzyme fixing film 42 so that the substance can be uniformly supplied to the surface of the electrode substrate 41, thereby achieving a high power. Especially with a biological fuel cell, the cavity S plays a very significant role because a fuel in use is often relatively high in viscosity with a low diffusion constant such as glucose.

Figure 19:
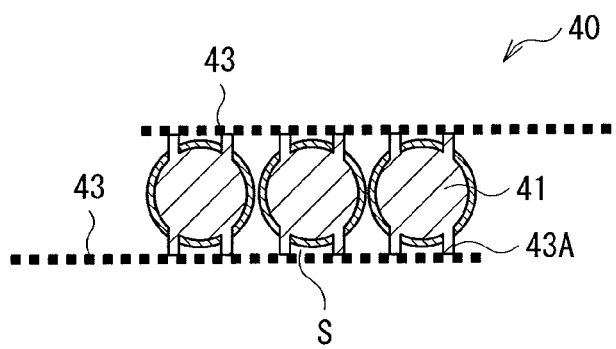
[FIG. 19] A cross sectional view of an enzyme electrode in another modified example.
Figure 20:
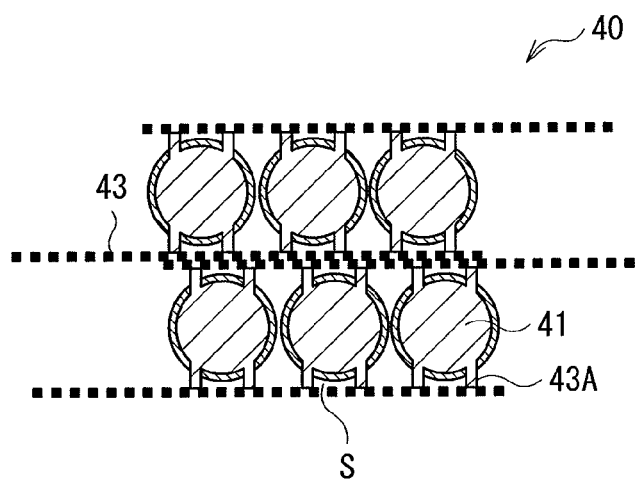
[FIG. 20] A cross sectional view of an enzyme electrode in still another modified example.

The current collector 43 may be plurally provided to one enzyme electrode 40. As shown in FIG. 19, the electrode substrates 41 may be sandwiched between two current collectors 43, or as shown in FIG. 20, a plurality of current collectors 43 may be provided to pass through a plurality of electrode substrates 41, for example.

The material for the current collector 43 is not specifically restrictive as long as it can establish an electrical connection with the outside, and any well-known raw materials can be freely selected for use therefor. The materials available for use are, for example, metal such as Pt, Ag, Au, Ru, Rh, Os, Nb, Mo, In, Ir, Zn, Mn, Fe, Co, Ti, V, Cr, Pd, Re, Ta, W, Zr, Ge, and Hf, alloys such as Alumel, brass, Duralumin, bronze, nickelin, platinum-rhodium, Hiperco, permalloy, permendur, nickel silver, and phosphor bronze, conductive polymer such as polyacethylene, carbon material such as graphite and carbon black, boride such as $HfB_2$, $NbB$, $CrB_2$, and $B_4C$, nitride such as $TiN$ and $ZrN$, silicide such as $VSi_2$, $NbSi_2$, $MoSi_2$, and $TaSi_2$, and a material being the combination thereof.

The enzyme electrode 40 described above can be used not only in the fuel cells 1, 21, and 31 in the first and second embodiments described above but also in a fuel cell 51 shown in FIG. 21, for example. This fuel cell 51 is provided with the enzyme electrode 40 configured by the electrode substrate 41, the enzyme fixing film 42, and the current collector 43 described above. The portion indicated by A in FIG. 21 corresponds to the enzyme electrode 40 shown in FIG. 18. The fuel cell 51 is provided with a fuel tank 52, a proton conductor 53, and others as required. In the below, the configuration, function, effects, and others are described for each of the components.

(1. Fuel Tank 52)

The fuel tank 52 is used for storage of a fuel. The fuel tank 52 is not specifically restricted in shape, and the shape is arbitrary as long as it can supply a fuel to an anode 40a (enzyme electrode). The method of supplying a fuel from the fuel tank 52 to the anode 40a is not also specifically restrictive, and any well-known methods can be freely selected for use therefor. For example, using the principles of injection with pressure, vacuum injection, contact absorption, capillary phenomenon, and others, the fuel can be supplied to the anode 40a.

The fuel of the fuel cell 51 is not specifically restrictive as long as it can emit electrons by an oxidation-reduction reaction with an enzyme used as a catalyst. Such a fuel is exemplified by a beverage such as juice, sports drink, sugar water, and alcohol, and cosmetics such as lotion. Specifically, for use as a fuel, those including sugar, protein, glycoprotein, fatty acid, or others are considered desirable.

(2. Proton Conductor 53)

Figure 21:
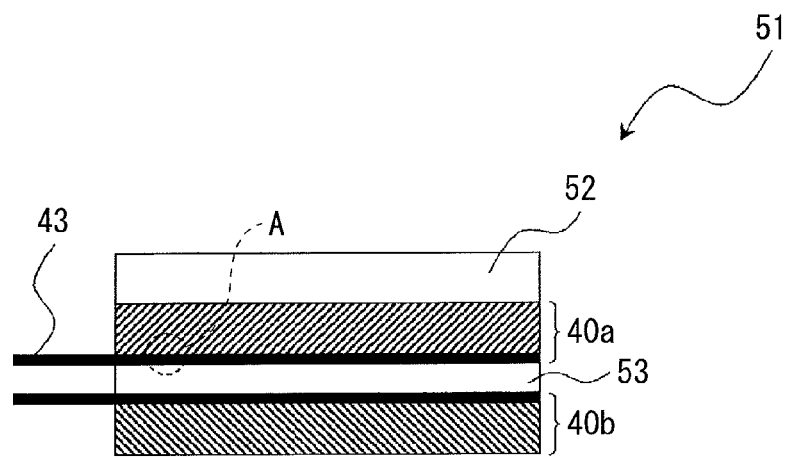
[FIG. 21] A cross sectional view of a fuel cell using the enzyme electrode of FIG. 18.

The anode 40a and a cathode 40b (enzyme electrode) are connected to each other in the state ready for conduction of protons. The method of connection is not specifically restrictive, but as shown in FIG. 21, for example, the anode 40a and the cathode 40b may be disposed to oppose each other with the proton conductor 53 sandwiched therebetween, thereby possibly establishing a connection between the anode 40a and the cathode 40b in the state ready for conduction of protons.

The material for the proton conductor 53 is not specifically restrictive as long as it is not electronically conductive and is electrolyte capable of transporting the H+, and any well-known materials can be selected for use therefor. As an example, an electrolyte material including a buffer substance can be used. The buffer substance can be exemplified by dihydrogen phosphate ion (H2PO4-) to be generated by sodium dihydrogen phosphate (NaH2PO4) or potassium dihydrogen phosphate (KH2PO4), 2-amino-2-hydroxymethyl-1,3-propanediol (abbreviated as tris), 2-(N-morpholino)ethanesulfonic acid (MES), cacodylic acid, carbonic acid (H2CO3), hydrogen citrate ion, N-(2-acetamide)iminodiacetic acid (ADA), piperazine-N,N'-bis(2-ethanesulfonic acid) (PIPES), N-(2-acetamide)-2-aminoethanesulfonic acid (ACES),3-(N-morpholino)propansulfonic acid (MOPS), N-2-hydroxyethyl piperazine-N'-2-ethanesulfonic acid (HEPES), N-2-hydroxyethyl piperazine-N'-3-propansulfonic acid (HEPPS), N-[tris(hydroxymethyl)methyl]glycin (abbreviated as tricine), glycylglycine, N,N-bis(2-hydroxyethyl)glycine (abbreviated as bicine), imidazole, triazole, a pyridine derivative, a bipyridine derivative, a compound containing an imidazole ring such as imidazole derivative (histidine, 1-methyl imidazole, 2-methyl imidazole, 4-methyl imidazole, 2-ethyl imidazole, imidazole-2-carboxylic acid ethyl, imidazole-2-carboxaldehyde, imidazole-4-carboxylic acid, imidazole-4,5-dicarboxylic acid, imidazole-1-yl-acetic acid, 2-acetyl benzimidazole, 1-acetylimidazole, N-acetylimidazole, 2-amino benzimidazole, N-(3-aminopropyl)imidazole, 5-amino-2-(trifluormethyl) benzimidazole, 4-azabenzimidazole, 4-aza-2-mercaptobenzimidazole, benzimidazole, 1-benzylimidazole, 1-butylimidazole), and others. Also nafion being a solid electrolyte material may be also used, for example.

Note that, in this embodiment, the proton conductor 53 is sandwiched between the two current collectors 43, but this is surely not restrictive. As an example, the current collector 43 may be disposed on the side of a plane opposite to the plane where the proton conductor 53 is disposed on the enzyme electrodes 40a and 40b. Still alternatively, a plurality of current collectors 43 may be provided to pass through a plurality of electrode substrates 41, for example.

(Electronic Device)

The fuel cell in the embodiments described above can lead to a high output current and voltage, and thus can be suitably used for any types of well-known electronic devices.

The electronic device is not specifically restricted in structure, function, and others as long as it is operated by a fuel cell, and includes every type of electrically-operating device, e.g., electronic devices such as cell phones, mobile devices, robots, personal computers, game machines, vehicle-mounted devices, consumer electronics equipments, and industry products, mobile units such as vehicles, motorcycles, airplanes, rockets, and spaceships, inspection equipments, power supply for pacemaker use, medical equipments such as power supply for in-body equipments including biosensor, power generation systems such as system of garbage decomposition for generation of electric energy, cogeneration systems, and others.

In the below, examples of such an enzyme electrode as described above are described.

Example 1

In an example 1, the enzyme electrode 40 described above was manufactured.

(1. Manufacturing of Current Collector)

As an exemplary current collector, used was a rolled sheet made of expanded metal including titanium. The rolled sheet made of expand metal as such was cut in many portions using a pinholder to form spike-like convex portions, thereby manufacturing a current collector with the convex portions. The convex portions had the average height of 0.1 to 1.0 mm.

(2. Manufacturing of Enzyme Fixing Film)

First of all, a porous carbon (PC) electrode (F) was prepared after coating of various types of solutions (A) to (E) and a conductive coating material (carbon material) in the following manner. A buffer solution for use of solution preparation was a buffer solution of 50 mM potassium dihydrogen phosphate (KH2PO4) (I.S.=0.3, and pH=7.5), and a buffer solution of 100 mM sodiumdihydrogenphosphate (NaH2PO4) (I.S.=0.3, pH=8.0).

(A) GDH/DI Enzyme Buffer Solution

DI (EC: 1.6.99, manufactured by Amano Enzyme Inc.) was weighed to be 47.6 mg, and was then dissolved into 200 μL of the buffer solution of 50 mM potassium dihydrogen phosphate (solution (A)'). For this process, the buffer solution for dissolving of the enzyme was preferably the one stored at the low temperature of 4° C. or lower immediately before the use, and the resulting enzyme-dissolved buffer solution was also preferably stored at the low temperature of 4° C. or lower if possible. Also in this embodiment, both the buffer solution and the enzyme-dissolved buffer solution were stored at the low temperature of 4° C. or lower.

GDH (NAD-dependent, EC: 1.1.1.47, manufactured by Amano Enzyme Inc.) was weighed to be 13.1 mg, and was then dissolved into 230 μL of the buffer solution of 100 mM sodiumdihydrogenphosphate described above. The resulting solution was added with 20 μm of the solution (A)' and then was mixed thoroughly, and the resulting solution was a GDH/DI enzyme-dissolved buffer solution (A).

(B) NADH Buffer Solution

NADH (manufactured by Sigma-Aldrich Japan, N-8129) was weighed to be 41 mg, and was then dissolved into 64 μL of the buffer solution of 100 mM sodiumdihydrogenphosphate described above. The resulting solution was an NADH buffer solution (B).

(C) ANQ Acetone Solution 2-amino-1,4-naphthoquinone (ANQ) (composition) was weighed to be 6.2 mg, and was then dissolved into 600 μL of an acetone solution. The resulting solution was an ANQ acetone solution (C).

(D) PLL Aqueous Solution poly-L-lycine hydrobromide (PLL) (manufactured by Sigma-Aldrich Japan, P-1274, Mw=93K) was weighed to be appropriate in amount, and was then dissolved into an ion-exchange water to have 2.0 wt %, and the resultant was a PLL aqueous solution (D).

(E) PAAcNA Aqueous Solution

Sodium polyacrylate (PAAcNa) (manufactured by Sigma-Aldrich Japan, 041-00595, Mw=30K) was weighed to be appropriate in amount, and was then dissolved into an ion-exchange water to have 0.022 wt %, and the resultant was a PAAcNa aqueous solution (E).

(F) Porous Carbon (PC) Electrode Coated with Conductive Coating (Carbon Material)

Varniphite being a conductive coating material (carbon material) (manufactured by Nippon Graphite Industries, ltd., Varniphite #27M) was diluted into 2-butanone (manufactured by Wako Pure Chemical Industries, Ltd., 133-02506) with a volume proportion of 5:1, and the resultant was coated on a porous carbon electrode (manufactured by Tokai Carbon Co., Ltd., 1 cm×1 cm×2 mm, 60% of voidage, about 95 to 98 mg) to be weighed about 105 to 108 mg after it was dried, and the resultant was then left for a night for drying (about 105 to 108 mg).

Next, the porous carbon electrode (F) coated with the conductive coating material was subjected to an ozone cleaning process on the upper and bottom surfaces each for 20 minutes. The solutions (A) to (C) prepared as above were mixed together each by the amount indicated in Table 1 below, and the resulting mixture was used to coat the porous carbon electrode through with the ozone cleaning process with a half amount each on the upper and bottom surfaces using a micropipette, for example. Thereafter, the resultant was dried in a dry oven for 15 minutes at 40° C. so that the manufacturing result was an enzyme-coenzyme-electron mediator-coated electrode.

TABLE 1

| GDH/DI Enzyme Buffer Solution (A) | 32 μL |
| NADH Buffer Solution (B) | 8.0 μL |
| ANQ Aceton Solution (C) | 74.8 μL |

Such an enzyme-coenzyme-electron mediator-coated electrode was coated with the PLL aqueous solution (D) on the upper and bottom surfaces each with a half of the amount in Table 2 below, and was then dried in the drive oven for 15 minutes at 40° C. The resulting electrode was then coated with the PAAcNa aqueous solution (E) on the upper and bottom surfaces each with a half of the amount in Table 2 below, and was then dried in the dry oven for 15 minutes at 40° C. As such, manufacturing result was an enzyme-coenzyme-electron mediator-fixed electrode

TABLE 2

| PLL Aqueous Solution (D) | 10 μL (total mass of PLL was 200 μg, and mass per projection area was 28.3 μg/mm$^2$) |
| PAAcNa Aqueous Solution (E) | 12 μL (total mass of PAAcNa was 2.64 μg, and mass per projection area was 374 ng/mm$^2$) |

(3) Measurement of Film Thickness of Enzyme Fixing Film

A plate-like glassy carbon electrode was disposed thereon with a sheet-like silicon rubber (thickness of 3.0 mm) formed with a circular hole having the diameter of 6 mm. The solutions (A) to (C) prepared as above were then mixed together each by the amount indicted in Table 3 below, and the resulting mixture was used to coat inside of the hole formed to the silicon rubber using a microsyringe. Thereafter, the resultant was dried in the dry oven for 15 minutes at 40° C. so that the manufacturing result was an enzyme-coenzyme-electron mediator-coated film inside of the hole of the silicon rubber.

TABLE 3

| GDH/DI Enzyme-Dissolved Buffer Solution (A) | 8.0 μL |
| NADH Buffer Solution (B) | 2.0 μL |
| ANQ Aceton Solution (C) | 18.7 μL |

On the enzyme-coenzyme-electron mediator-coated film manufactured inside of the hole of the silicon rubber, the PLL aqueous solution (D) was coated by the amount indicated in Table 2 above, and then the resultant was dried in the dry oven for 15 minutes at 40° C. Thereafter, the PAAcNa aqueous solution (E) was coated by the amount indicated in Table 2 described above, and then the resultant was dried in the dry oven for 15 minutes at 40° C. so that the manufacturing result was an enzyme fixing film.

The silicon rubber was then removed with full attention not to peel away the enzyme fixing film formed on the glassy carbon electrode (inside of the hole of the silicon rubber), and by using a stylus profilometer (Dektak3, SLOAN THE CHNOLOGY), this enzyme fixing film was measured for its film thickness. As a result, the measured film thickness was about 40 to 80 μm.

Example 2

In an example 2, the value of a torque was changed for clamping in a unipolar evaluation cell to check how the resistance value of an electrode showed a change by the enzyme fixing film.

Figure 22:
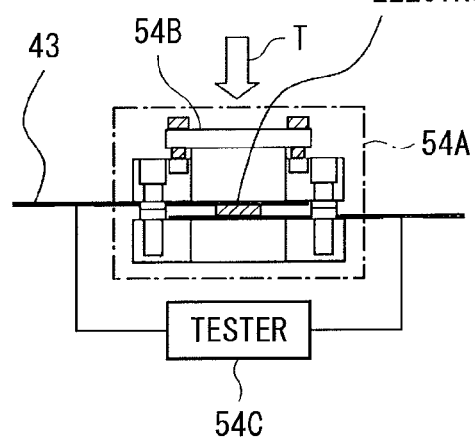
[FIG. 22] A schematic illustration of a torque generation device.
Figure 23:
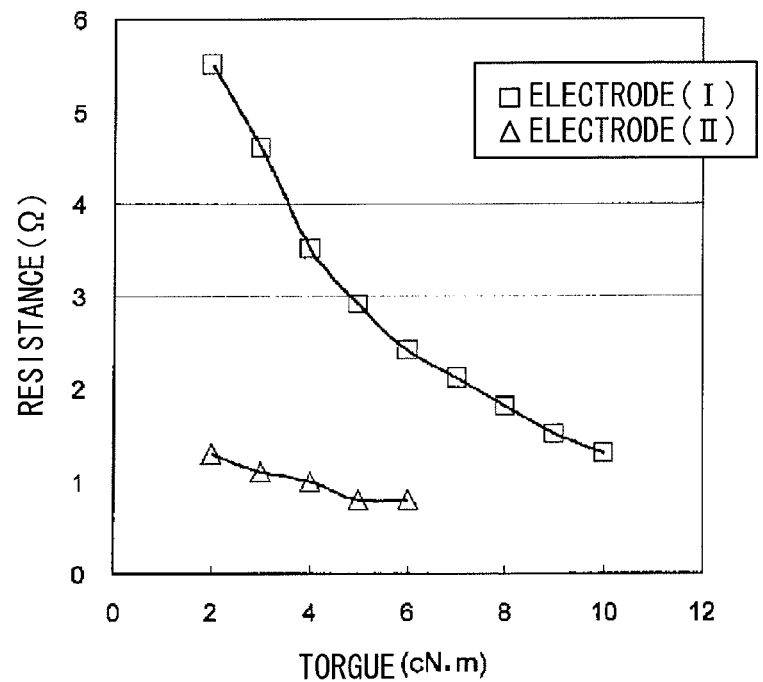
[FIG. 23] A characteristics diagram showing the relationship between a torque and a resistance value in an example 2.

Prepared were the porous carbon electrode (F) manufactured in the example 1 with coating of the conductive coating material ("electrode (I)" in this example), and the enzyme-fixing-film electrode (electrode (II)) manufactured in the example 1. Each of the electrodes was set on a unipolar evaluation cell 54A, and a rolled sheet made of expand metal using titanium was disposed on both the upper and bottom surfaces of the electrode. Then in a torque generation device shown in FIG. 22, the resistance value between the two current collectors 43 was measured using a tester 54C while the torque was being changed for clamping on an upper lid 54B. The result is shown in FIG. 23.

The electrode (I) was known to show a decrease of resistance value in accordance with the torque. On the other hand, the electrode (II) showed a much larger resistance value compared with that of the electrode (I), but was known to show a decrease of resistance value also in accordance with the torque similarly to the electrode (I). From the result, it was found that, in a biological fuel cell using an electrode provided with an enzyme fixing film, the resistance value is larger than that in a general fuel cell.

Example 3

In an example 3, the contact resistance between the surface of an electrode substrate and a current collector was checked to see whether it was decreased by a convex portion of the current collector. In other words, from the check result in the example 1 about the torque and the resistance value, it was found that when an electrode substrate in use is the one provided with an enzyme fixing film, the contact resistance between the electrode substrate and the current collector is the issue. In consideration thereof, the contact resistance was checked to see whether it can be reduced if a current collector in use was formed with a convex portion.

One enzyme-fixing-film electrode manufactured in the example 1 was set on a unipolar evaluation cell, and a flat rolled sheet made of expanded metal (current collector (a)) was disposed on both the upper and bottom surfaces of an electrode, and a current collector (b) formed in the example 1 with the convex portion was disposed on both the upper and bottom surfaces of another electrode. These electrodes were each clamped on the upper lid with a torque of 2 cN·m using the torque generation device shown in FIG. 22. The resistance values thereof were each measured using a tester 54. The results are shown in Table 4.

As shown in Table 4, compared with a case of using the current collector (a) in a general biological fuel cell, using a current collector (b) formed with the convex portion was known to extremely reduce the resistance value between the upper and bottom surfaces of the electrode substrate.

TABLE 4

| Current Collector | (a) No Convex Portion | (b) With Convex Portion |
|---|---|---|
| Resistance Value | 5.5 Ω | 0.7 Ω |

Example 4

In an example 4, the effects of reducing a contact resistance when the current collector (b) in use was provided with the convex portion were checked electrochemically.

Figure 26:
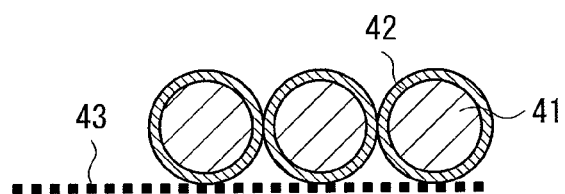
[FIG. 26] A cross sectional view of an enzyme electrode in a comparison example.
Figure 27:
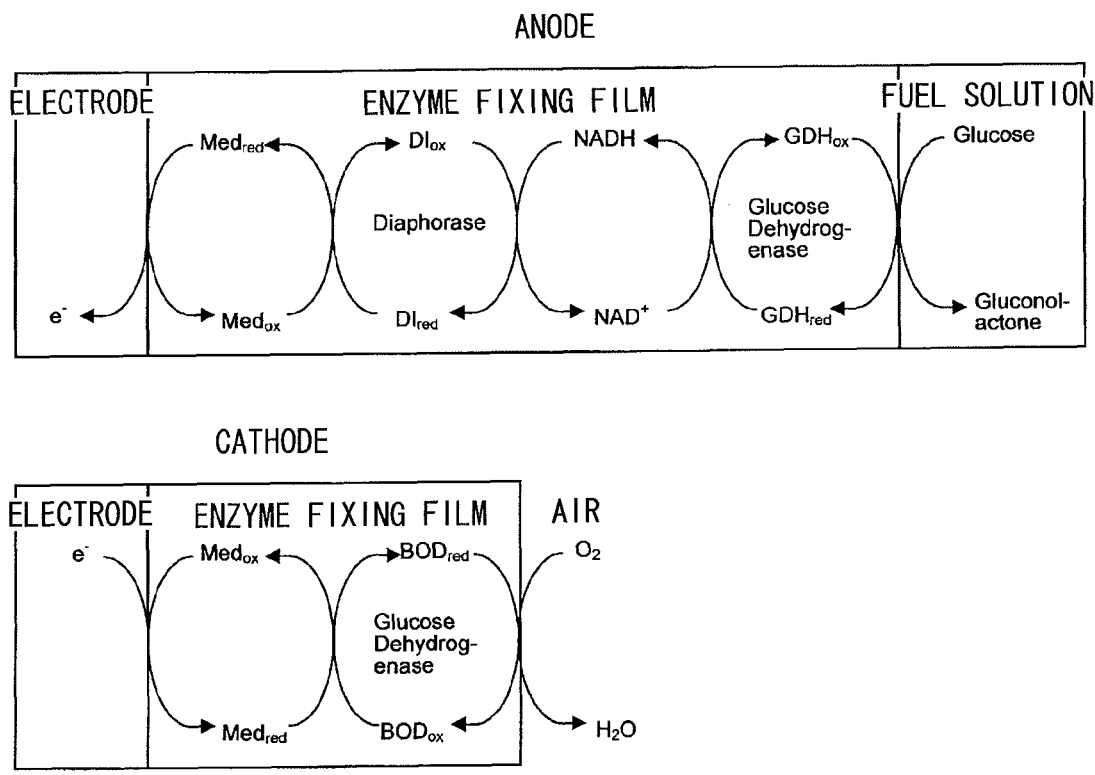
[FIG. 27] A diagram showing a reaction scheme of an enzyme electrode.
Figure 28:
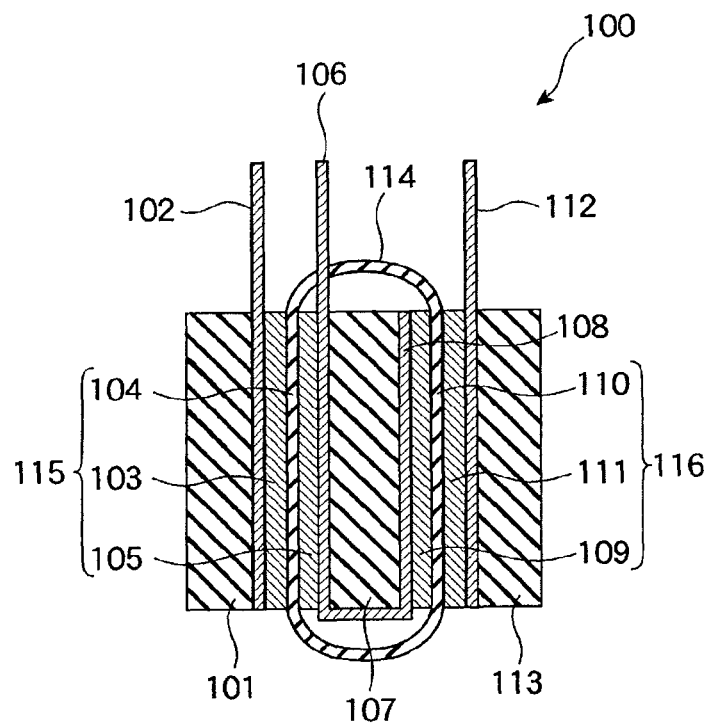
[FIG. 28] A cross sectional view of a previous fuel cell, showing the configuration thereof.

First of all, one enzyme-fixing-film electrode manufactured in the example 1 was set on a unipolar evaluation cell, and a flat rolled sheet made of expanded metal (current collector (a)) was disposed on both the upper and bottom surfaces of an electrode, and a current collector (b) formed in the example 1 with the convex portion was disposed on both the upper and bottom surfaces of another electrode. These electrodes were each clamped on the upper lid with a torque of 2 cN·m using the device shown in FIG. 22. The current collector (b) formed with the convex portion is the one shown in FIG. 18, and the current collector (a) not formed with the convex portion is the one corresponding to the one shown in FIG. 26.

Next, as a fuel solution, by using a solution prepared by dissolving glucose varying in concentration as 0M, 0.2M, 0.4M, 0.6M, 1.0M, and 2.0M in a buffer of 2.0M imidazole-hydrochloric acid (ph 7.0), the LSV (linear sweep voltammetry) measurement (−0.6 to −0.1V, 1mV/s) was taken place. The results are shown in FIGS. 24 and 25.

Figure 24:
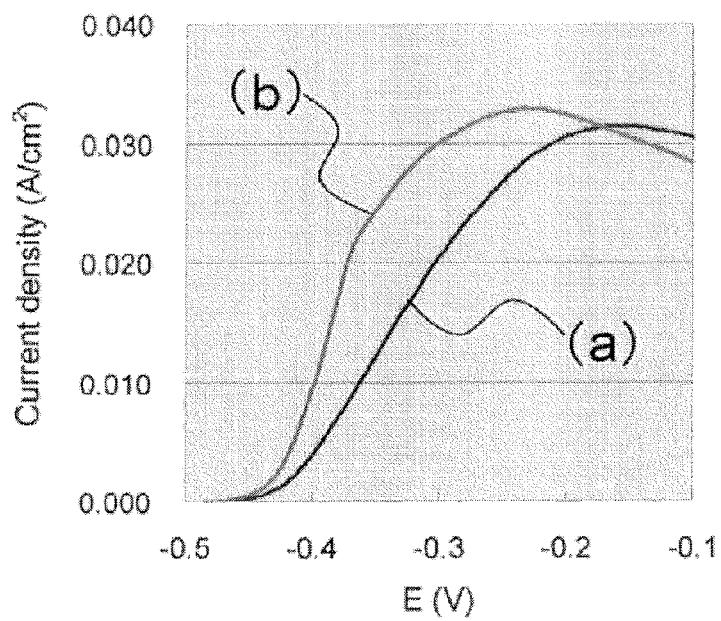
[FIG. 24] A characteristics diagram showing the result of an LSV measurement (glucose 0.4M) in an example 4.
Figure 25:
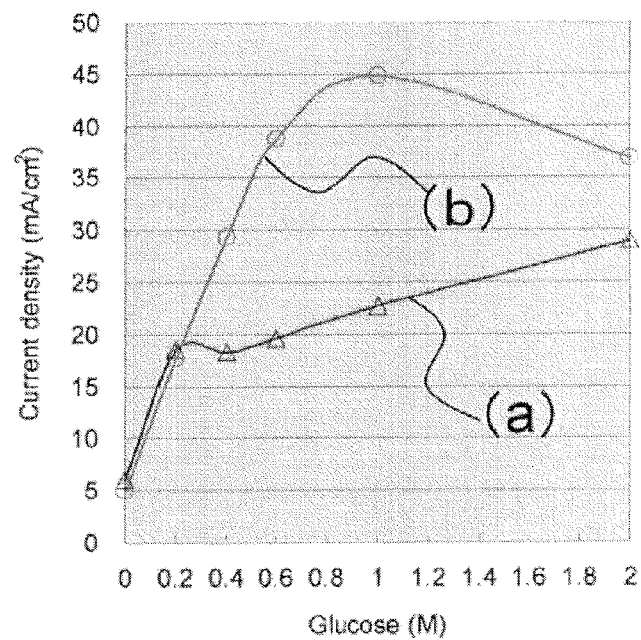
[FIG. 25] A characteristics diagram showing the result of a comparison (between a current collector (a) and a current collector (b)) about a concentration dependence of glucose with the current density of −0.3V in the LSV in the example 4.

FIG. 24 is a diagram showing the result of the LSV measurement (glucose 0.4M) in the case of using the current collectors (a) and (b). FIG. 25 shows the comparison result (between the current collectors (a) and (b)) about the glucose concentration dependence with the current density of −0.3V in the LSV.

By referring to FIG. 24, it was known that the case of using the current collector (b) provided with the convex portion shows a large slope at the beginning of the LSV. By referring to FIG. 25, it was known that the current collectors (a) and (b) show almost no difference until the glucose concentration reaches about 0.2M, but once the concentration exceeds 0.2M, the case of using the current collector (b) provided with the convex portion shows an extremely high current density.

From the results, it was found that, by using the current collector (b) provided with the convex portion, the contact resistance can be remarkably reduced between the electrode substrate formed with the enzyme fixing film and the current collector, and the substance transport of glucose is also performed better so that the current density can be high.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:
1. A fuel cell comprising:
a cathode;
an anode disposed opposite to the cathode; and
a proton conductor sandwiched between the anode and the cathode,
wherein each of the anode and the cathode comprises:
an electrode substrate;
an enzyme fixing film for fixedly providing an enzyme to the electrode substrate; and
a current collector provided with a convex portion higher than a thickness of the enzyme film, wherein the current collector comes in contact with the electrode substrate by the convex portion.
2. The fuel cell according to claim 1, wherein the cathode is at least partially water-repellent on a surface thereof.
3. The fuel cell according to claim 1, further comprising:
a terminal for a connection use with another fuel cell;
a fuel supply hole to supply a fuel into the fuel cell; and
an exhaust hole to exhaust gas from the fuel cell, wherein each of the terminal, the fuel supply hole, and the exhaust hole are disposed on a different plane.
4. The fuel cell according to claim 3, further comprising:
a fuel guidance section for guiding the fuel provided by the fuel supply hole at a predetermined position of a fuel tank and/or in a predetermined direction.
5. The fuel cell according to claim 3, wherein one or more magnets are internally provided, and the terminal is connected to another by a magnetic force.
6. The fuel cell according to claim 1, wherein the fuel cell is a coin-shaped or tube-shaped cell.

7. The fuel cell according to claim 1, wherein a cavity is formed between the enzyme fixing film and the current collector.

8. The fuel cell according to claim 1, wherein at least one of the anode or the cathode is fixedly provided with an oxidoreductase for use as a catalyst.

9. The fuel cell according to claim 1, wherein the anode is configured by fixedly providing an oxidoreductase and an electron mediator on a surface of an electrode made of a conductive porous material.

10. The fuel cell according to claim 9, wherein the conductive porous material comprises a carbon material, wherein the carbon material comprises one of porous carbon, carbon pellet, carbon felt, carbon paper, carbon fiber, or carbon-particle laminate.

11. The fuel cell according to claim 1, wherein the cathode is configured by fixedly providing an oxidoreductase and an electron mediator on a surface of an electrode made of a conductive porous material.

12. The fuel cell according to claim 11, wherein the conductive porous material comprises a carbon material, wherein the carbon material comprises one of porous carbon, carbon pellet, carbon felt, carbon paper, carbon fiber, or carbon-particle laminate.

13. The fuel cell according to claim 11, wherein the electron mediator comprises one of ferrocyanide, potassium ferricyanide, or potassium octacyanotungstate.

14. The fuel cell according to claim 1, wherein an aqueous solution of poly-L-lysine (PLL) and polyacrylic acid (PAAc) is used as the enzyme fixing film for fixedly providing the enzyme to an electrode surface.

15. The fuel cell according to claim 1, wherein the cathode is configured by a plurality of electrodes each disposed with a space from one another.

16. The fuel cell according to claim 8, wherein the oxidoreductase comprises one of bilirubin oxidase, laccase, or ascorbate oxidase.

* * * * *